United States Patent [19]
Alfano et al.

[11] Patent Number: 6,091,983
[45] Date of Patent: *Jul. 18, 2000

[54] IMAGING OF OBJECTS IN TURBID MEDIA BASED UPON THE PRESERVATION OF POLARIZED LUMINESCENCE EMITTED FROM CONTRAST AGENTS

[76] Inventors: Robert R. Alfano, 3777 Independence Ave., Bronx, N.Y. 10463; Stavros G. Demos, 32-72 30 St., Astoria, N.Y. 11106; Wubao Wang, 138-10 Franklin Ave., Apt. 5B, Flushing, N.Y. 11355

[*] Notice: This patent issued on a continued prosecution application filed under 37 CFR 1.53(d), and is subject to the twenty year patent term provisions of 35 U.S.C. 154(a)(2).

[21] Appl. No.: 08/797,027

[22] Filed: Feb. 7, 1997

Related U.S. Application Data

[60] Provisional application No. 60/030,054, Nov. 6, 1996.

[51] Int. Cl.[7] .................................................. A61B 5/00
[52] U.S. Cl. ........................ 600/431; 600/475; 600/477; 250/341.3; 356/364; 356/433
[58] Field of Search ..................................... 600/431, 425, 600/476, 477, 473, 475; 356/317, 318, 337, 338, 364, 369, 370, 432, 433; 250/341.3

[56] References Cited

PUBLICATIONS

Demos et al., "Temporal gating in highly scattering media by the degree of optical polarization," Optics Letters, 21(2):161–3 (Jan. 15, 1996).

Demos et al., "Time resolved degree of polarization for human breast tissue," Optics Communications 124:439–42 (Mar. 15, 1996).

Huang et al., "Optical Coherence Tomography," Science, 254:1178–81 (1991).

Yoo et al., "Imaging objects hidden in scattering media using a fluorescence–absorption technique," Optics Letters, 16(16):1252–4 (1991).

Denk et al., "Two–Photon Laser Scanning Fluorescence Microscopy," Science, 248:73–6 (1990).

Masters et al., Ultraviolet confocal fluorescence microscopy of the in vitro cornea: redox metabolic imaging, Applied Optics, 32(4)592–6 (1993).

*Primary Examiner*—Ruth S. Smith
*Attorney, Agent, or Firm*—Kriegsman & Kriegsman

[57] ABSTRACT

A method and system for imaging an object in a turbid medium. According to one embodiment, the method involves (a) making the object luminescent by adding to the object a contrast agent of the type that emits at least partially polarized light when appropriately excited with polarized radiation; (b) exciting the luminescent object through the turbid medium with polarized radiation so as to cause luminescent light to be emitted from the luminescent object, the luminescent light initially being at least partially polarized; (c) after the luminescent light has emerged from the turbid medium, the luminescent light consisting of a ballistic component, a snake-like component and a diffuse component, detecting a pair of complementary polarization components of the luminescent light; and (d) forming an image of the object using the pair of complementary polarization components.

41 Claims, 22 Drawing Sheets

IMAGING OF OBJECTS IN TURBID MEDIA BASED UPON THE PRESERVATION OF POLARIZED LUMINESCENCE EMITTED FROM CONTRAST AGENTS

CROSS-REFERENCE TO RELATED APPLICATIONS

The present application claims the benefit under 35 U.S.C. § 119(e) of U.S. Provisional Patent Application Ser. No. 60/030,054, filed Nov. 6, 1996, in the names of Robert R. Alfano, Stavros G. Demos and Wubao Wang.

BACKGROUND OF THE INVENTION

The present invention relates generally to methods for imaging objects located in turbid media and more particularly to a novel method for imaging objects located in turbid media.

As can readily be appreciated, there are many situations in which the detection of an object present in a turbid, i.e., highly scattering, medium is highly desirable. For instance, the detection of a tumor embedded within a tissue is one such example. Although X-ray techniques do provide some measure of success in detecting objects in turbid media, they are not typically well-suited for detecting very small objects, e.g., tumors less than 1 mm in size embedded in tissues, or for detecting objects in thick media. In addition, X-ray radiation can present safety hazards to a person exposed thereto. Ultrasound and magnetic resonance imaging (MRI) offer alternatives to the use of X-rays but have their own drawbacks.

Another technique used to detect objects in turbid media, such as tumors in tissues, is transillumination. In transillumination, visible light is incident on one side of a medium and the light emergent from the opposite side of the medium is used to form an image. Objects embedded in the medium typically absorb the incident light and appear in the image as shadows. Unfortunately, the usefulness of transillumination as a detection technique is severely limited in those instances in which the medium is thick or the object is very small. This is because light scattering within the medium contributes to noise and reduces the intensity of the unscattered light used to form the image shadow.

To improve the detectability of small objects located in a turbid medium using transillumination, many investigators have attempted to selectively use only certain components of the transilluminating light signal. This may be done by exploiting the properties of photon migration through a scattering medium. Photons migrating through a turbid medium have traditionally been categorized into three major signal components: (1) the ballistic (coherent) photons which arrive first by traveling over the shortest, most direct path; (2) the snake (quasi-coherent) photons which arrive within the first δt after the ballistic photons and which deviate, only to a very slight extent, off a straight-line propagation path; and (3) the diffusive (incoherent) photons which experience comparatively more scattering than do ballistic and snake photons and, therefore, deviate more considerably from the straight-line propagation path followed by ballistic and snake photons.

Because it has been believed that ballistic and snake photons contain the least distorted image information and that diffusive photons lose most of the image information, efforts to make transillumination work most effectively with turbid media have traditionally focused on techniques which involve the preferential detection of ballistic and snake photons over diffusive photons. The preferential selection of ballistic and snake photons over diffusive photons has traditionally been implemented by using various time-gating, space-gating and time/space-gating techniques. Patents and publications which disclose certain of these techniques include U.S. Pat. No. 5,140,463, inventors Yoo et al., which issued Aug. 18, 1992; U.S. Pat. No. 5,143,372, inventors Alfano et al., which issued Aug. 25, 1992; U.S. Pat. No. 5,227,912, inventors Ho et al., which issued Jul. 13, 1993; U.S. Pat. No. 5,371,368, inventors Alfano et al., which issued Dec. 6, 1994; Alfano et al., "Photons for prompt tumor detection," *Physics World*, pp. 37–40 (January 1992); Wang et al., "Ballistic 2-D Imaging Through Scattering Walls Using an Ultrafast Optical Kerr Gate," *Science*, Vol. 253, pp. 769–771 (Aug. 16, 1991); Wang et al., "Kerr-Fourier imaging of hidden objects in thick turbid media," *Optics Letters*, Vol. 18, No. 3, pp. 241–243 (Feb. 1, 1993); Yoo et al., "Time-resolved coherent and incoherent components of forward light scattering in random media," *Optics Letters*, Vol. 15, No. 6, pp. 320–322 (Mar. 15, 1990); Chen et al., "Two-dimensional imaging through diffusing media using 150-fs gated electronic holography techniques," *Optics Letters*, Vol. 16, No. 7, pp. 487–489 (Apr. 1, 1991); Duncan et al., "Time-gated imaging through scattering media using stimulated Raman amplification," *Optics Letters*, Vol. 16, No. 23, pp. 1868–1870 (Dec. 1, 1991), all of which are incorporated herein by reference.

Of the above-listed art, Wang et al., "Kerr-Fourier imaging of hidden objects in thick turbid media," *Optics Letters*, Vol. 18, No. 3, pp. 241–243 (Feb. 1, 1993) is illustrative. In this article, there is disclosed a time/space-gating system for use in imaging opaque test bars hidden inside a 5.5 cm-thick 2.5% Intralipid solution. The disclosed system includes three main parts: a laser source, an optical Kerr gate and a detector. The laser source is a picosecond mode-locked laser system, which emits a 1054 nm, 8 ps laser pulse train as the illumination source. The second harmonic of the pulse train, which is generated by transmission through a potassium dihydrate phosphate (KDP) crystal, is used as the gating source. The illumination source is sent through a variable time-delay and is then used to transilluminate, from one side, the turbid medium containing the opaque object. The signal from the turbid medium located at the front focal plane of a lens is collected and transformed to a Kerr cell located at its back focal plane (i.e., the Fourier-transform spectral plane of a 4F system). That portion of the Kerr cell located at the focal point of the 4F system is gated at the appropriate time using the gating source so that only the ballistic and snake components are permitted to pass therethrough. The spatial-filtered and temporal-segmented signal is then imaged by a second lens onto a CCD camera.

Another technique for preferentially detecting ballistic and snake photons, as opposed to diffusive photons, for use in transillumination is described in co-pending U.S. patent application Ser. No. 08/573,939, filed Dec. 18, 1995, in the names of Robert R. Alfano et al, the disclosure of which is incorporated herein by reference. More specifically, the aforementioned application discloses a method and apparatus for imaging and/or characterizing a tissue based upon the extent to which initially polarized light maintains its polarization after propagating through the tissue. Said method and apparatus are based in part on the discovery that, when initially polarized light is transmitted through a turbid medium, such as human tissue, the ballistic and snake-like components of the light emergent from the turbid medium maintain the polarization of the initially polarized light while the diffuse component of the light emergent from the turbid medium becomes completely depolarized. In a preferred embodiment, said application teaches a method for imaging an object located in or behind a turbid medium which comprises the steps of (a) illuminating the object through the turbid medium with a pulse of light, the pulse of light being polarized and having an initial state of polarization, whereby light consisting of a ballistic component, a snake-like component and a diffuse component emerges from the illuminated turbid medium; (b) passing the emergent light from the illuminated turbid medium through a polarizing means which is alternately oriented parallel to the initial state of polarization of the pulse of light and perpendicular to the initial state of polarization of the pulse of light so as to enable the measurement of the parallel and perpendicular polarization components of the emergent light; (c) detecting the parallel and perpendicular polarization components of the emergent light; (d) subtracting the perpendicular polarization component from the parallel polarization component to yield a difference; and (e) forming an image of the object using said difference.

Still another technique for improving the quality of a transillumination image of an object hidden in a turbid medium is described in Yoo et al., "Imaging objects hidden in scattering media using a fluorescence-absorption technique," Optics Letters, 16(16):1252–4 (Aug. 15, 1991), which is incorporated herein by reference. More specifically, the aforementioned publication discloses a transillumination imaging technique wherein an object hidden in a scattering medium is made luminescent by the addition thereto of a contrast agent, and luminescent light emitted from the contrast agent is selected for imaging while the illuminating light is filtered out. The technique is based in part on the observation that, as illuminating light traverses through a highly scattering medium, its signal intensity (containing the image information) decreases whereas its multiply scattered light intensity (containing noise) decreases. The technique is further based in part on the observation that one way to reduce the amount of noise from the multiply scattered light is to shorten the distance the signal light traverses in the turbid medium. In accordance with said technique, such a shortening of the distance traversed by the light signal is achieved by making the object luminescent and then viewing the luminescent light. The quality of the image can be further improved by introducing an absorbing dye into the turbid medium that preferentially absorbs the luminescent light from the contrast agent. In this manner, because the multiply scattered light travels over a longer path length than the ballistic signal, the multiply scattered light is attenuated more than the signal light by absorption.

In addition to being used in the aforementioned manner, contrast agents have also been used in connection with a variety of different medical imaging techniques (e.g., X-ray, PGT, and CAT tomography) to enhance image quality and to increase the quantity of information obtained. The polarization properties of fluorescent light emitted by several contrast agents, such as Eosin, Rose Begal and TCTIF in non-turbid media, have been studied using picosecond time-dependent fluorescence measurements. See Fleming et al., "Direct observation of rotational diffusion by picosecond spectroscopy," Chem. Phys., 17:91–100 (1976) and Porter et al., "Picosecond rotational diffusion in kinetic and steady state fluorescence spectroscopy," Chem. Phys. Lett., 49:416–20 (1977), both of which are incorporated herein by reference. The results of such studies show that the aforementioned contrast agents, when photoexcited by polarized light, emit partially polarized light, keeping the preferred polarization of the pump light.

Accordingly, in view of the above, it can readily be appreciated that there is an outstanding need for a high resolution subsurface imaging technique adapted for use with turbid media. Imaging techniques employing optical coherence tomography (Huang et al., "Optical coherence tomography," Science, 254:1178–81 (1991)), confocal microscopy (Masters et al., "Ultraviolet confocal fluorescence microscopy of the in vitro cornea: redox metabolic imaging," Appl. Opt., 32:592–6 (1993)) and two-photon excitation microscopy (Denk et al., "Two-photon laser scanning fluorescence microscopy," Science, 248:73–6 (1990)) have been developed and do provide high resolution subsurface images; however, such techniques are limited by the fact that the imaging depth is small, i.e., on the order of about 1 mm or less.

SUMMARY OF THE INVENTION

It is an object of the present invention to provide a novel method for imaging an object located in a turbid medium.

It is another object of the present invention to provide a method for imaging an object located in a turbid medium that overcomes at least some of the drawbacks associated with existing methods for imaging objects located in turbid media.

The present invention makes use of the following two principles: (1) that the ballistic and snake components of polarized light retain at least some of their initial polarization as they travel through a turbid medium whereas the diffuse component of polarized light becomes randomly polarized as it travels through a turbid medium and (2) that certain contrast agents emit at least partially polarized luminescent light when photoexcited with polarized light, the partially polarized luminescent light keeping the preferred polarization direction of the photoexciting pump light.

According to one aspect, the present invention relates to a method for imaging an object located in a turbid medium, said method comprising the steps of: (a) making the object luminescent by adding to the object a contrast agent of the type that emits at least partially polarized light when appropriately excited; (b) exciting the luminescent object through the turbid medium with polarized radiation so as to cause luminescent light to be emitted from the luminescent object, said luminescent light initially being at least partially polarized; (c) after said luminescent light has emerged from the turbid medium, said luminescent light consisting of a ballistic component, a snake-like component and a diffuse component, detecting a pair of complementary polarization components of said luminescent light; and (d) forming an image of the object using the pair of complementary polarization components.

Preferably, the illuminating radiation is linearly polarized light, the pair of complementary polarization components are parallel and perpendicular to the illuminating light and said forming step comprises subtracting the perpendicular component from the parallel component to yield a difference and using said difference to form said image.

The contrast agent of the present invention, instead of being of the type that emits at least partially polarized luminescent light upon illumination with polarized light, may also be of the type that emits polarized luminescent light regardless of whether the illuminating light is polarized. In the case of said latter type of contrast agent, the present invention relates to a method for imaging an object located in a turbid medium, said method comprising the steps of: (a) making the object luminescent by adding to the object a contrast agent of the type that emits polarized light when appropriately excited; (b) exciting the luminescent object through the turbid medium with radiation so as to cause luminescent light to be emitted from the luminescent object, said luminescent light consisting of a ballistic component, a snake-like component and a diffuse component, said luminescent light initially being polarized; (c) after said luminescent light has emerged from the turbid medium, detecting a pair of complementary polarization components of said luminescent light; and (d) forming an image of the object using the pair of complementary polarization components.

The present invention is also directed to a system for performing the above-described methods.

Additional objects, features, aspects and advantages of the present invention will be set forth in part in the description which follows, and in part will be obvious from the description or may be learned by practice of the invention. Various embodiments of the invention will be described in sufficient detail to enable those skilled in the art to practice the invention, and it is to be understood that other embodiments may be utilized and that changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 1:
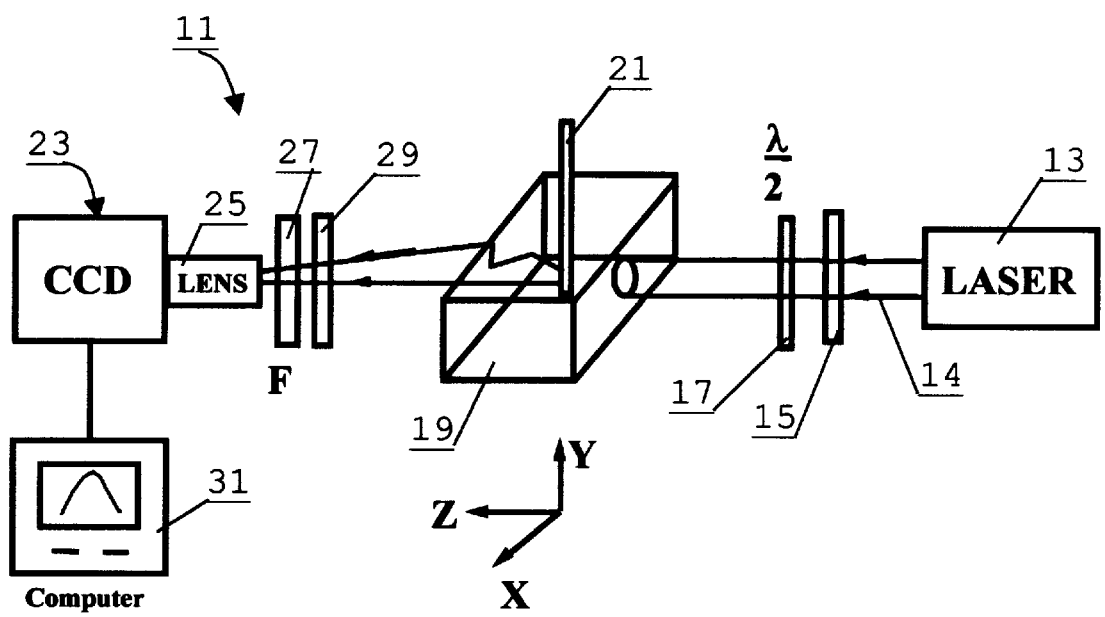
FIG. 1 is a schematic view of a first embodiment of a system for imaging an object in a turbid medium, the system being constructed according to the teachings of the present invention.

The present invention is directed to a novel method for imaging an object located in a turbid medium. As noted above, the present invention makes use of the following principles: (1) that the ballistic and snake components of initially polarized light maintain their polarization as they travel through a turbid medium whereas the diffuse component of initially polarized light loses its polarization as it travels through a turbid medium; and (2) that certain contrast agents emit at least partially polarized luminescent light when photoexcited with pump light, some of said contrast agents emitting polarized luminescent light regardless of whether the pump light is polarized, other of said contrast agents emitting partially polarized luminescent light only when the pump light is polarized, the partially polarized luminescent light keeping the preferred polarization of the pump light.

According to a first embodiment, said method comprises the steps of (a) making the object luminescent by adding to the object a contrast agent of the type that emits at least partially polarized light when excited with polarized radiation; (b) exciting the luminescent object through the turbid medium with polarized radiation, whereby luminescent light is emitted from the luminescent object, said luminescent light initially being at least partially polarized; (c) after said luminescent light has emerged from the turbid medium, said luminescent light consisting of a ballistic component, a snake-like component and a diffuse component, detecting a pair of complementary polarization components of said luminescent light; and (d) forming an image of the object using the pair of complementary polarization components.

The illuminating polarized radiation can be in the form of pulsed or continuous wave light (lamp or laser), X-rays or particle beam. Preferably, the illuminating polarized radiation is either continuous wave or pulsed light. Preferably, the illuminating polarized light is a pulse of linearly polarized light, and the pair of complementary polarization components are parallel and perpendicular to the illuminating polarized light. Said forming step preferably comprises forming one of a ratio, a difference or a combination ratio and difference of the perpendicular and parallel components of the luminescent light so as to minimize the effect of the diffuse component of the luminescent light. Examples of said ratio, difference or combination include, for example, $I_\parallel - I_\perp$, $I_\parallel / I_\perp$, $(I_\parallel - I_\perp)/(I_\parallel + I_\perp)$, $(I_\perp)/(I_\parallel - I_\perp)$, $(I_\parallel - I_\perp)/(I_\perp)$, and $(I_\parallel - I_\perp)/(I_\parallel)$.

According to a second embodiment, said method comprises the steps of (a) making the object luminescent by adding to the object a contrast agent of the type that emits polarized light when excited; (b) exciting the luminescent object through the turbid medium with radiation, whereby luminescent light is emitted from the luminescent object, said luminescent light initially being polarized; (c) after said luminescent light has emerged from the turbid medium, said luminescent light consisting of a ballistic component, a snake-like component and a diffuse component, detecting a pair of complementary polarization components of said luminescent light; and (d) forming an image of the object using the pair of complementary polarization components.

The method of the present invention can be combined with other imaging techniques to further enhance image clarity and volume of information and can be used in the fields of optical imaging, optical tomography and optical mammography.

Referring now to FIG. 1, there is schematically shown an experimental set-up of a system constructed according to the teachings of the present invention for imaging an object in a turbid medium, the system being represented generally by reference numeral 11.

System 11 comprises a laser source 13. In the present embodiment, laser source 13 comprises a mode-locked Nd:YAG laser operating at a repetition rate of 82 MHz for emitting a laser beam 14, laser beam 14 being expanded to a 3-cm diameter and comprising a series of second harmonic laser pulses at 532 nm. System 11 also comprises a polarizer 15 for ensuring that laser beam 14 is linearly polarized and a half-wave plate 17 for alternating the polarization direction of laser beam 14 along either the x-axis or the y-axis shown in FIG. 1.

System 11 also includes a 7×5×5 cm$^3$ glass cell 19, glass cell 19 containing a scattering medium in the form of intralipid solution. Positioned in the middle of cell 19 and oriented along the y-axis is a 1-mm diameter pipette 21. Pipette 21, which is disposed along the path of beam 14, is filled with Eosin, a contrast agent, at a concentration of 1×10$^{-4}$ M diluted in $C_2H_5OH$. Eosin strongly absorbs at 532 nm and emits in the 570–640 nm spectral region with an emission peak at 580 nm. When illuminated with linearly polarized light, Eosin emits light that is partially polarized, the ratio between the parallel and perpendicular polarization components being approximately 1.2 to 1, respectively.

System 11 further includes a CCD camera 23 located 40 cm from pipette 21 on the opposite side of cell 19 relative to laser source 13. The zoom lens 25 in front of camera 23 is set to image in the x,y plane the light emitted from pipette 21. A holographic notch filter 27 at 532 nm and a linear polarizer 29 are positioned in front of lens 25. Notch filter 27 is used to cut off the illuminating light so that only the luminescent emission from the contrast agent is recorded by CCD camera 23, and polarizer 29 is set in one direction (y-axis) so as to selectively pass either only the parallel component or only the perpendicular component of the luminescent light, the particular polarization component passed depending upon the setting of half-wave plate 17.

System 11 further includes a computer 31, which is coupled to CCD camera 23 to receive the output therefrom. Computer 31 subtracts the perpendicular component of the luminescent light detected by CCD camera 23 from the parallel component of the luminescent light detected by CCD camera 23 and displays a difference image. (Instead of calculating a difference between the parallel and perpendicular components, computer 31 could alternatively calculate a ratio or a combination ratio/difference that has the similar effect of minimizing the contribution to the readings of diffuse light.)

Although not wishing to be limited to any particular theory of the invention, the principles behind the operation of system 11 are believed to be as follows: Recently, it has been shown that, when a polarized light pulse propagates in a scattering medium, the emerging pulse is partially polarized over the initial 100 ps. See Demos et al., *Opt. Lett.*, 21:161 et seq. (1996); and Demos et al., *Opt. Commun.*, 124:439 et seq. (1996), both of which are incorporated herein by reference. Accordingly, when polarized light pulses from beam 14 travel through the turbid medium of glass cell 19 and reach pipette 21, they are still partially polarized. The contrast agent within pipette 21 absorbs the partially polarized light and emits light photons which are also partially polarized. The polarized portion of the emitted light decreases as it travels through the turbid medium; nevertheless, a small portion of the light that emerges from the turbid medium is still polarized. The photons that retain their initial polarization after traveling through the turbid medium are those that scattered less while traveling through the turbid medium (i.e., the ballistic and snake components). These polarized photons contain the image information of the light emitting pipette to a higher degree than do the diffusive photons, which constitute the main component of the emerging light. As a result, subtraction of the two polarization image components recorded by the CCD camera leads to an image formed by the still-polarized photons.

Figure 2A:
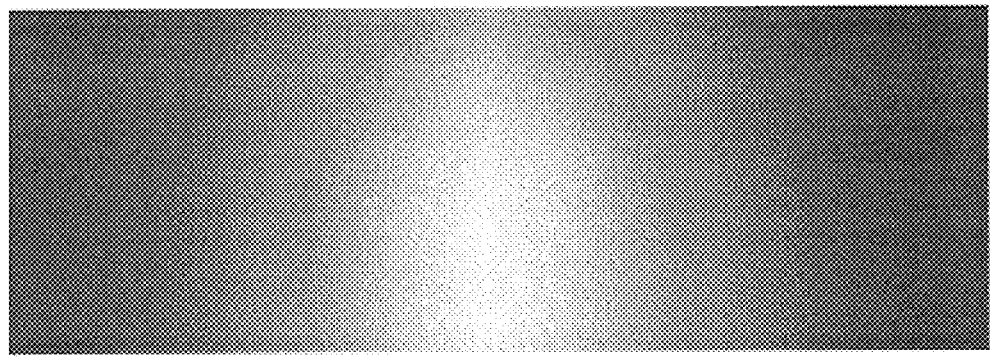
FIGS. 2(a) through 2(c) are images obtained using the system of FIG. 1 of a 1-mm pipette filled with a luminescent contrast agent and positioned within a quantity of 0.08% intralipid solution, the images being formed of (a) the parallel component of the luminescent light, (b) the perpendicular component of the luminescent light and (c) the difference of the parallel and perpendicular components of the luminescent light, respectively.
Figure 2B:
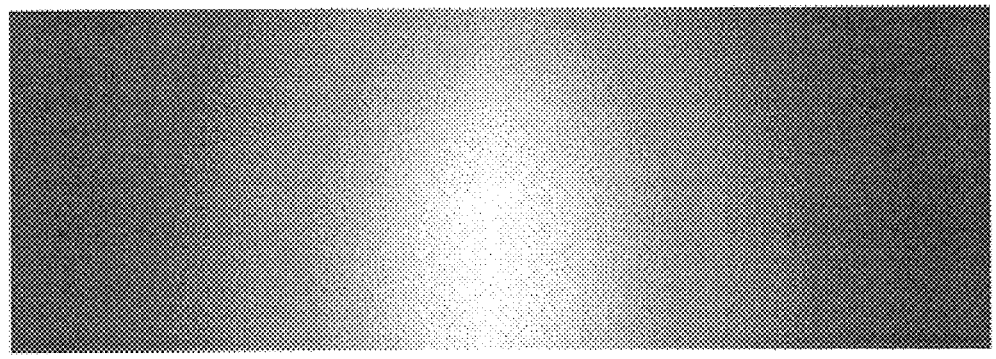
Figure 2C:
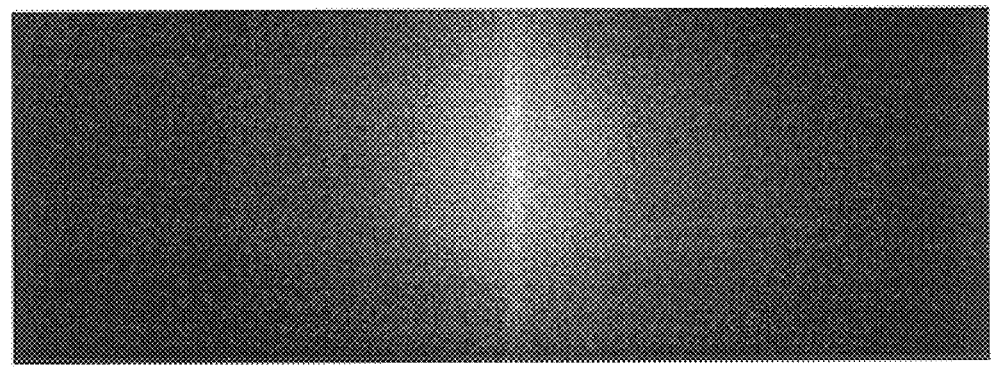
Figure 2:
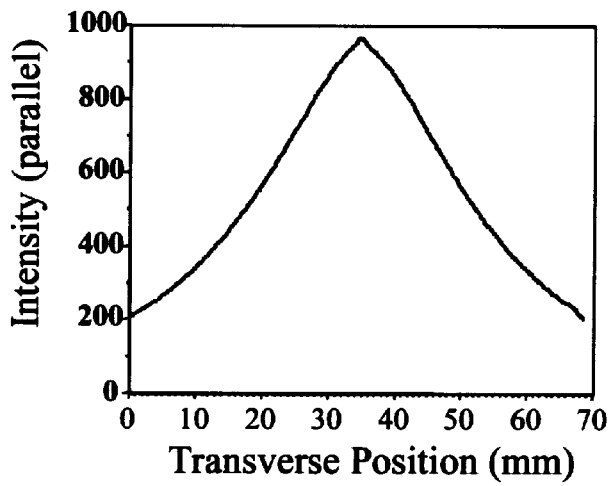
FIGS. 2(d) through 2(f) are digitized intensity profiles across a horizontal line at the center of the images of FIGS. 2(a) through 2(c), respectively.
Figure 2:
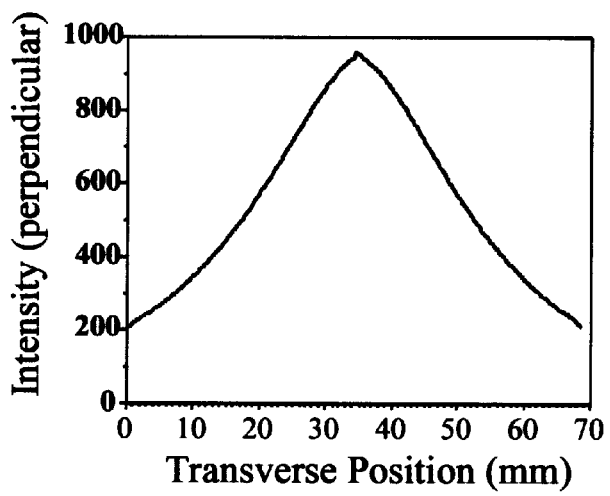
Figure 2:
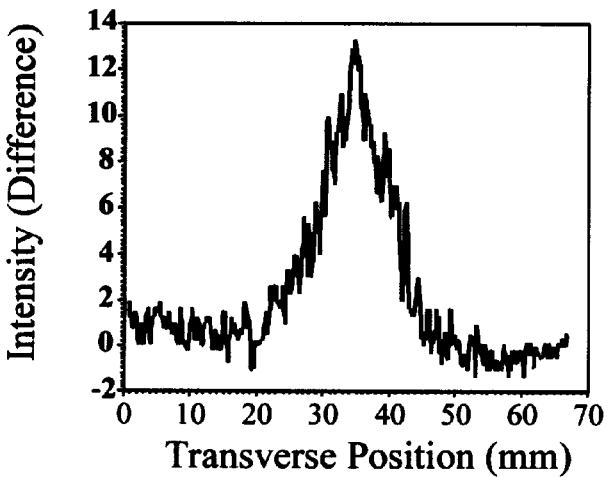

Referring now to FIGS. 2(*a*) through 2(*c*), one can see the improvement in image quality obtained using the method of the present invention. FIG. 2(*a*) is an image of a 1 mm pipette in 0.08% intralipid solution obtained using system 11, with polarizer 29 parallel to the polarization of beam 14. FIG. 2(*b*), by comparison, is an image obtained using system 11, with polarizer 29 perpendicular to the polarization of beam 14. The images of FIGS. 2(*a*) and 2(*b*) appear to have no observable major differences, except that the intensity of the parallel image (FIG. 2(*a*)) is approximately 1% higher than the intensity of the perpendicular image (FIG. 2(*b*)) at the center of the image (i.e., near the line). However, an image of the difference in intensity between the parallel and perpendicular components (FIG. 2(*c*)) is very different from the images of the parallel and perpendicular components by themselves, particularly at the center of the image. The concentration of the intralipid solution in glass cell 19 was chosen so that only a very small portion of the light emitted by the contrast agent within pipette 21 would not undergo scattering. Those photons that did not undergo scattering, i.e., the ballistic photons, contributed to the formation of the slightly brighter line in the middle of the image shown in FIGS. 2(*a*) and 2(*b*), which is a direct image of the contrast agent-containing pipette. In FIG. 2(*c*), the direct image of the pipette is enhanced with respect to the intensity of the rest of the image. In addition, in FIG. 2(*c*), the intensity is confined to the area near the line at the center of the image. The above observations are verified in FIGS. 2(*d*) through 2(*f*), where the digitized intensity profiles of FIGS. 2(*a*) through 2(*c*), respectively, are shown across a horizontal line at the center of the images of FIGS. 2(*a*) through 2(*c*). It may be noted that the difference profile (FIG. 2(*f*)) has an intensity approximately 1% of the intensity of the parallel (FIG. 2(*d*)) and perpendicular (FIG. 2(*e*)) image components.

Figure 3:
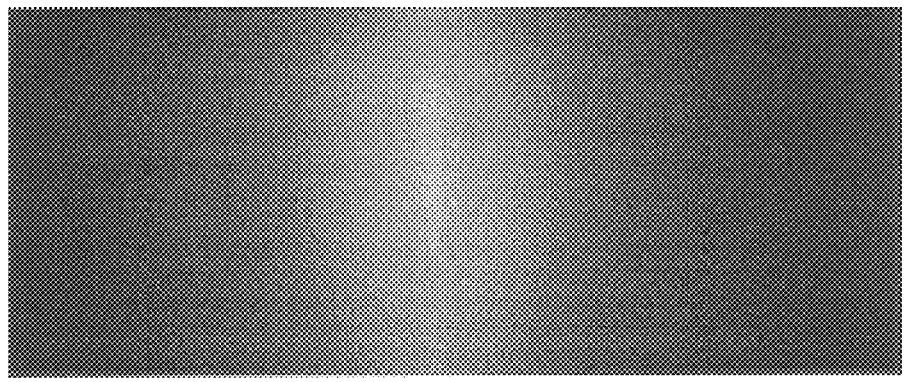
FIGS. 3(a) through 3(c) are images obtained using the system of FIG. 1 of a 1-mm pipette filled with a luminescent contrast agent and positioned within a quantity of 0.08% intralipid solution and Malachite Green absorbing dye, the images being formed of (a) the parallel component of the luminescent light, (b) the perpendicular component of the luminescent light and (c) the difference of the parallel and perpendicular components of the luminescent light, respectively.
Figure 3:
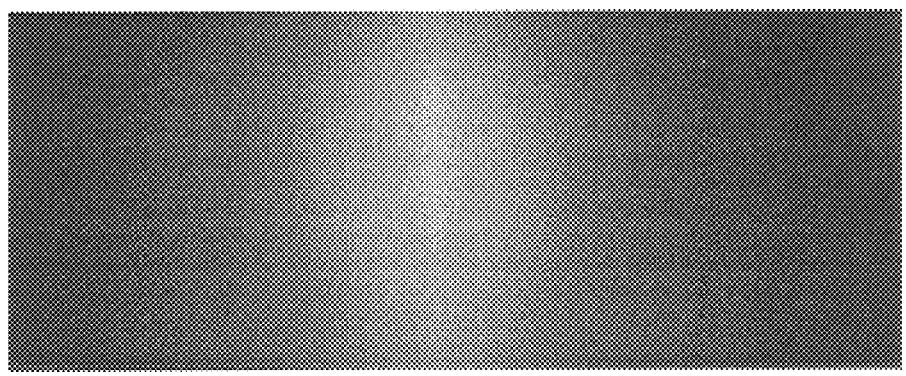
Figure 3:
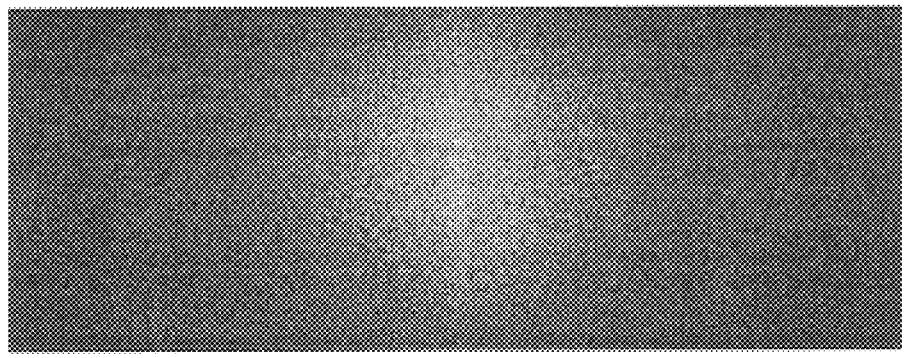

As discussed above, it is known that the addition of a luminescence-absorbing dye to a highly scattering medium containing a luminescent object improves the image of the luminescent object due to the greater absorption of the diffuse component of the luminescent light than of the ballistic and snake components of the luminescent light. To determine if a similar improvement could be obtained in connection with the present method, we introduced the contrast agent Malachite Green to the scattering medium and obtained images of the parallel component (FIG. 3(*a*)), the perpendicular component (FIG. 3(*b*)) and the difference between the parallel and perpendicular components (FIG. 3(*c*)) in the same manner as described above for FIGS. 2(*a*) through 2(*c*), respectively. The concentration of Malachite Green was set to a level where the best possible image quality was achieved. As can be seen by comparing FIG. 3(*a*) to FIG. 3(*b*), the difference in intensity between the two polarization image components was approximately 1%. Subtraction of the two polarization components of FIGS. 3(*a*) and 3(*b*) led to an image (FIG. 3(*c*)) that was slightly improved in quality relative to FIGS. 3(*a*) and 3(*b*).

Figure 4:
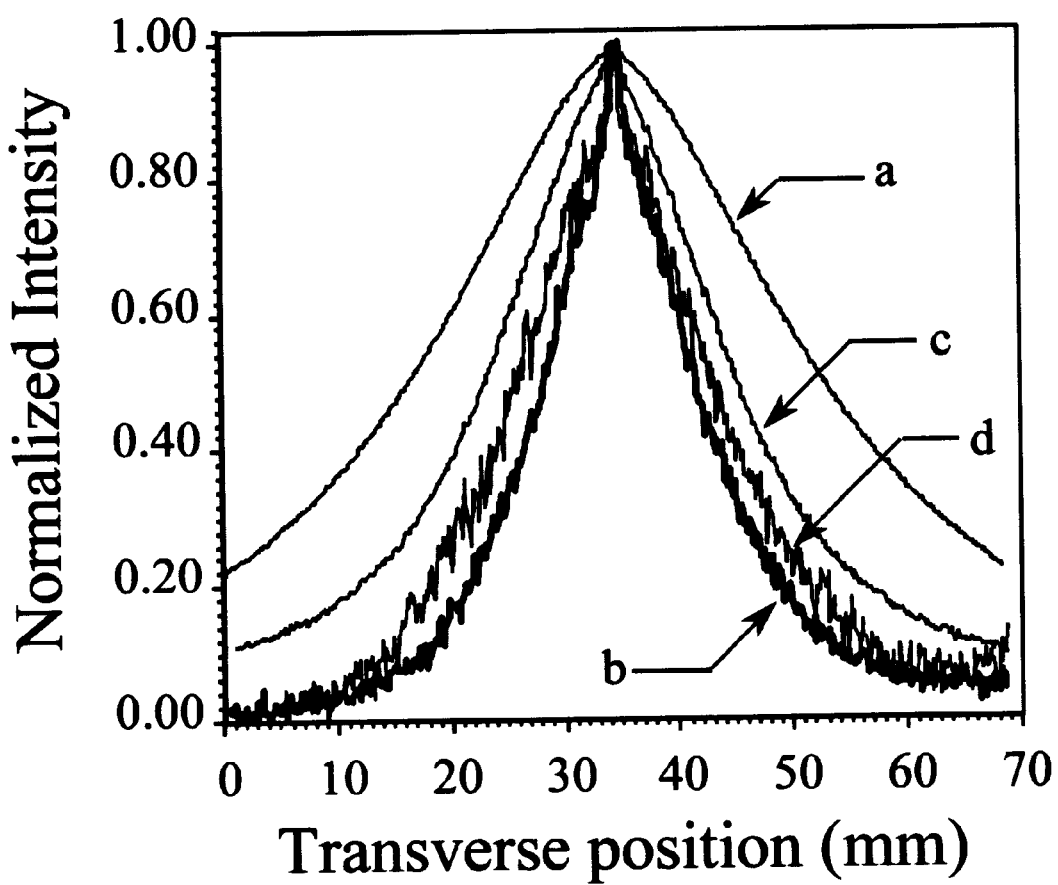
FIG. 4 is. a graphic representation of the digitized normalized image intensity profiles of the images of FIGS. 2(a), 2(c), 3(a) and 3(c)

Referring now to FIG. 4, there are shown the digital normalized intensity profiles of the images displayed in FIGS. 2(*a*), 2(*c*), 3(*a*) and 3(*c*). Profiles (a) and (b) represent the intensity profiles in the transverse position of the parallel polarization image of FIG. 2(*a*) and the polarization difference image of FIG. 2(*c*), respectively. Profiles (c) and (d) represent the intensity profiles of the parallel polarization image of FIG. 3(*a*) and the polarization difference image of FIG. 3(*c*), respectively. As can be seen, the worst image quality, with poor resolution, is that exhibited by profile (a), which represents the image obtained when no polarization or fluorescence absorption was used for image improvement. As demonstrated by profile (c), the addition of a fluorescence absorbing dye to the scattering medium resulted in some improvement in the image quality. However, the best image quality was achieved using the polarization difference imaging technique of profile (b), where the FWHM resolution reduces to approximately ⅓ of its original value. In the case where the fluorescence absorbing dye was added to the scattering medium and polarization difference imaging was used, profile (d), some improvement in image quality could be observed relative to that obtained when only the parallel polarization component was used, both with (profile (c)) and without (profile (a)) the addition of the fluorescence absorbing dye. Nevertheless, the similar resolutions of profiles (b) and (d) indicate that the introduction of the fluorescence absorbing dye did not result in any further improvement in the quality of the polarization difference image.

Figure 5A:
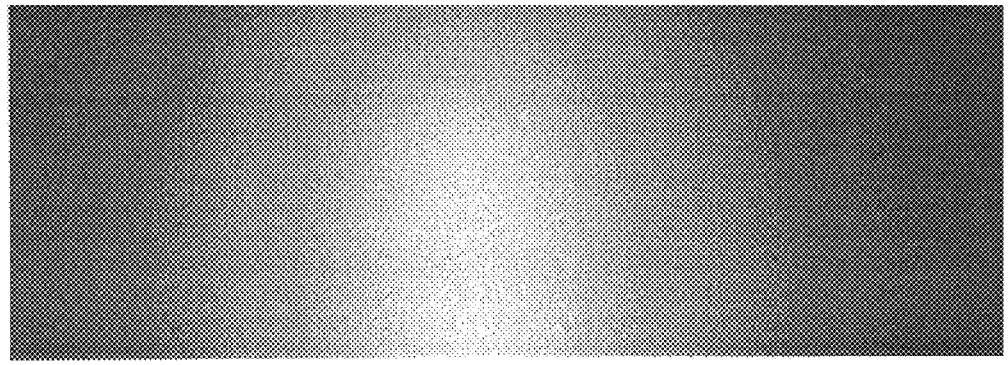
FIGS. 5(a) through 5(c) are images obtained using the system of FIG. 1 of a 1-mm pipette filled with a luminescent contrast agent and positioned within a quantity of 0.09% intralipid solution, the images being formed of (a) the parallel component of the luminescent light, (b) the perpendicular component of the luminescent light and (c) the difference of the parallel and perpendicular components of the luminescent light, respectively.
Figure 5B:
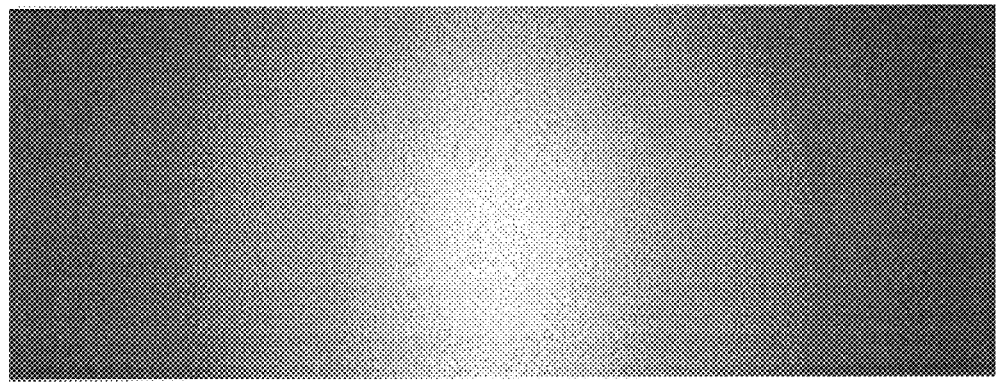
Figure 5C:
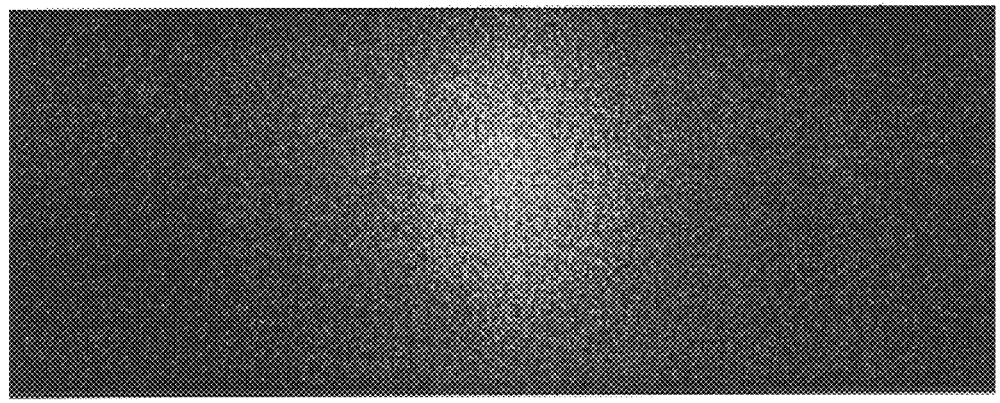

Referring now to FIGS. 5(*a*) through 5(*c*), there are shown images obtained using the system of FIG. 1 of the same Eosin-filled pipette now positioned within a quantity of 0.09% intralipid solution, the images being formed of (a) the parallel component of the luminescent light, (b) the perpendicular component of the luminescent light and (c) the difference of the parallel and perpendicular components of the luminescent light, respectively. With the concentration of the intralipid solution set at 0.09%, virtually none of the ballistic photons emitted from the contrast agent reach the detector. As can be seen, the parallel and perpendicular component images of FIGS. 5(*a*) and 5(*b*), respectively, differ from their corresponding images of FIGS. 2(*a*) and 2(*b*) (obtained under lesser scattering conditions) in that the brighter line in the middle of each image of FIGS. 5(*a*) and 5(*b*) is missing due to the absence therein of ballistic photons. By comparison, the polarization difference image of FIG. 5(*c*) shows a marked improvement in image quality.

Figure 6:
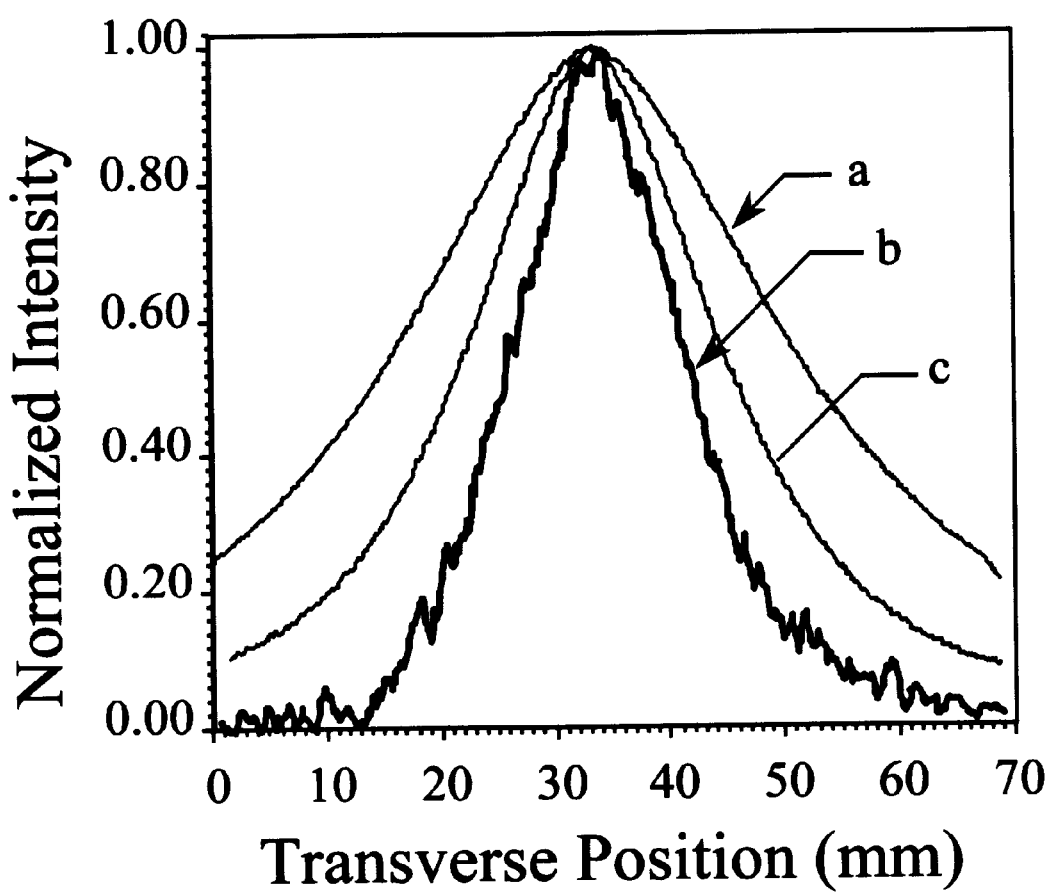
FIG. 6 is a graphic representation of the digitized normalized image intensity profiles of the images of FIGS. 5(a), 5(c) and of the parallel polarization image obtained when the fluorescence absorbing dye Malachite Green was added to the turbid medium of FIG. 5(a)

Referring now to FIG. 6, there are shown the digital normalized intensity profiles of the images displayed in FIGS. 5(*a*) and 5(*c*), profile (a) representing the intensity profile in the transverse position of the parallel polarization image of FIG. 5(*a*) and profile (b) representing the polarization difference image of FIG. 5(*c*). In addition, profile (c) of FIG. 6 represents the intensity profile of a parallel polarization image obtained when the fluorescence absorbing dye Malachite Green was added to the 0.09% intralipid solution. As can be seen, an approximately threefold improvement in image quality was obtained when the difference between the parallel and perpendicular components was used to image the object. Without wishing to be limited to any particular theory behind the invention, the present inventors believe that this improvement in image quality can be explained as follows: (1) the contrast agent Eosin emits partially polarized luminescent light; and (2) the subtraction of the perpendicular component from the parallel component substantially eliminates the diffusion effect to the signal image.

As can readily be appreciated, one requirement of the present invention is that the object wished to be imaged be luminescent and that the luminescent light emitted from the object be at least partially polarized. This requirement can be achieved by making the object luminescent by the addition thereto of a contrast agent of the type that emits partially polarized light when photoexcited with polarized light. Eosin, Rose Begal and TCTIF, Cardio Green, photofrin, HPD and porphyrin derivative dyes are examples of such a contrast agent. Other such contrast agents include certain dyes, phosphors, dielectrics, ceramics, semiconductors, and impurity doped materials, such as Eu-doped and Cr-doped powders. Preferably, the contrast agent emits optical radiation in the spectral region between 400 and 1600 nm. In addition, where the present technique is used to image diseased tissues, the contrast agent preferably exhibits an affinity for such diseased tissues (e.g., cancerous tissues).

The above-discussed requirement that the object emit at least partially polarized light can be met by the addition to the object of a contrast agent of the type that emits polarized light when photoexcited, regardless of whether the photoexciting light is itself polarized. Still another way in which this requirement can be met is by selecting an object that, even without the use of a contrast agent, inherently emits at least partially polarized luminescent light when photoexcited. For any of the above alternatives, the luminescent object preferably emits polarized light with an optical relaxation time in the range of 50 ps to 5 $\mu$s.

The technique of the present invention has many applications, one such application being medical imaging. For example, as alluded to above, by administering to a patient a contrast agent that preferentially bind to cancerous tumors and that also emits at least partially polarized luminescent light when appropriately photoexcited (e.g., hematoporphyrin derivative (HPD)), one can image the luminescent light so as to detect cancer. Such a technique could be used to detect tumors, for example, in the brain, breast, prostate, liver or kidney.

Figure 7:
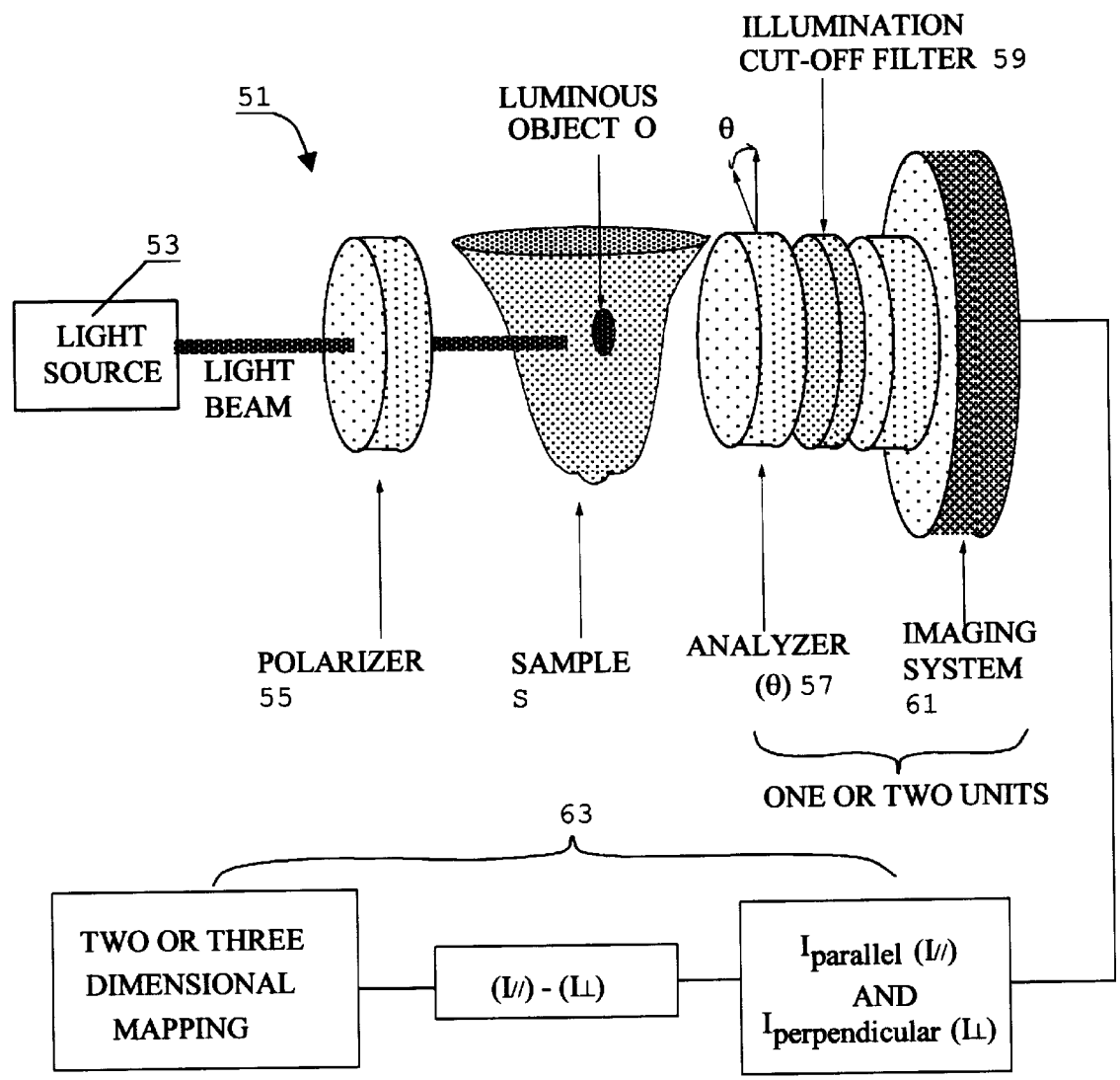
FIG. 7 is a schematic view of a second embodiment of a system for imaging an object in a turbid medium, the system being constructed according to the teachings of the present invention.

Referring now to FIG. 7, there is shown a schematic view of a second embodiment of a system for imaging an object in a turbid medium, the system being constructed according to the teachings of the present invention and represented generally by reference numeral 51.

System 51 includes a light source 53, which may be the same as laser 13 of system 11 and which is used to illuminate a luminous object O in a sample S. System 51 also includes a linear polarizer 55, which is used to ensure that the beam of light emitted from light source 53 and used to illuminate the luminous object O is polarized. System 51 further includes an analyzer 57, a filter 59 and an imaging system 61, which are arranged in a transmission geometry on the opposite side of the sample. Analyzer 57 is rotatably mounted to alternately pass the parallel and perpendicular polarization components of the transmitted light. Filter 59, which may take the form of a holographic notch, is designed to block the transmission of the illuminating light and to allow the transmission of the luminescent polarized light. Imaging system 61, which may be, for example, a CCD camera, detects the light passed through filter 59 and converts the light signals into electrical signals.

System 51 further includes electronics and computer software 63 coupled to imaging system 61 for processing the electrical signals transmitted therefrom and for providing one, two or three dimensional mapping of the sample.

Figure 8:
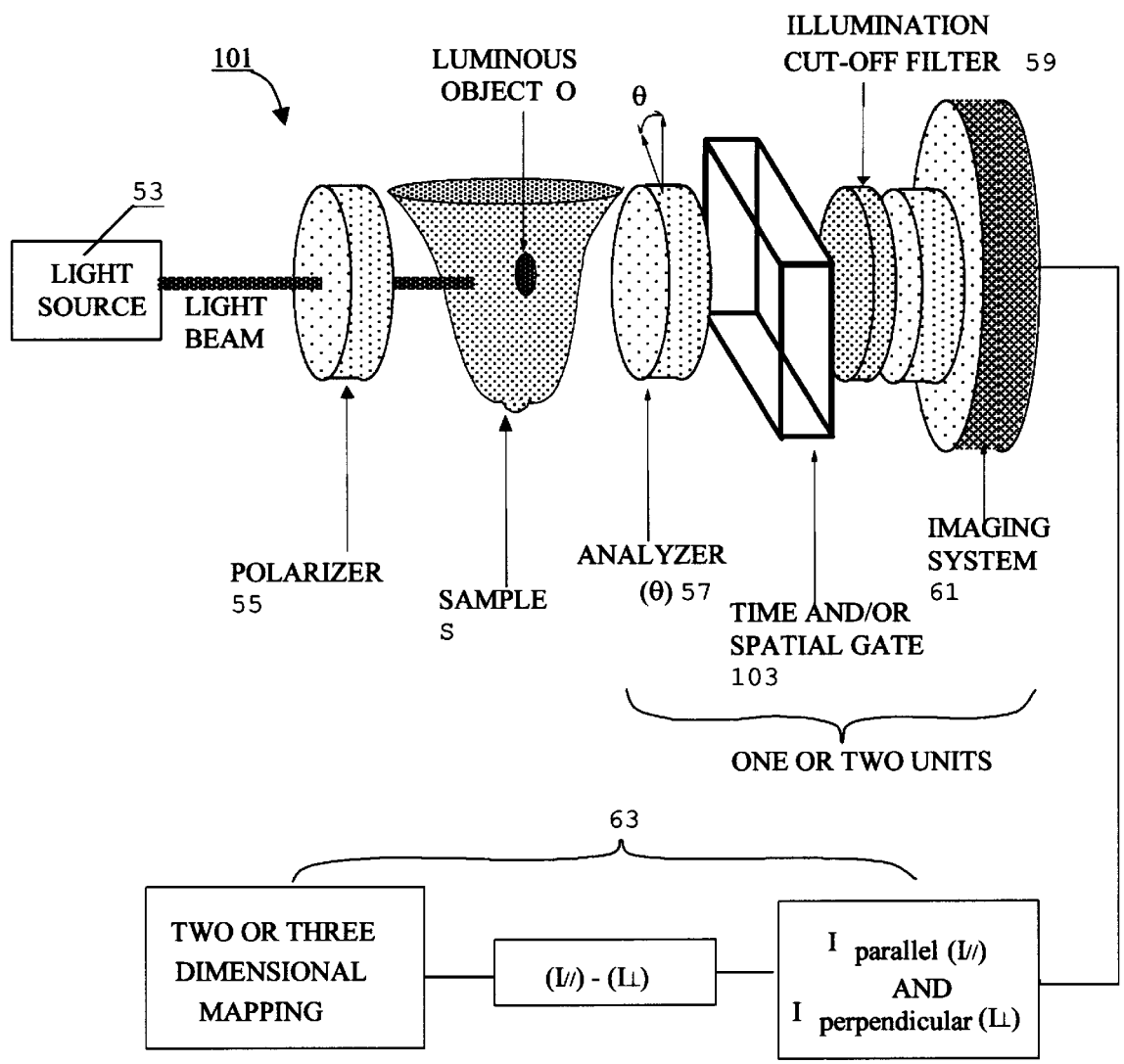
FIG. 8 is a schematic view of a third embodiment of a system for imaging an object in a turbid medium, the system being constructed according to the teachings of the present invention.
Figure 9:
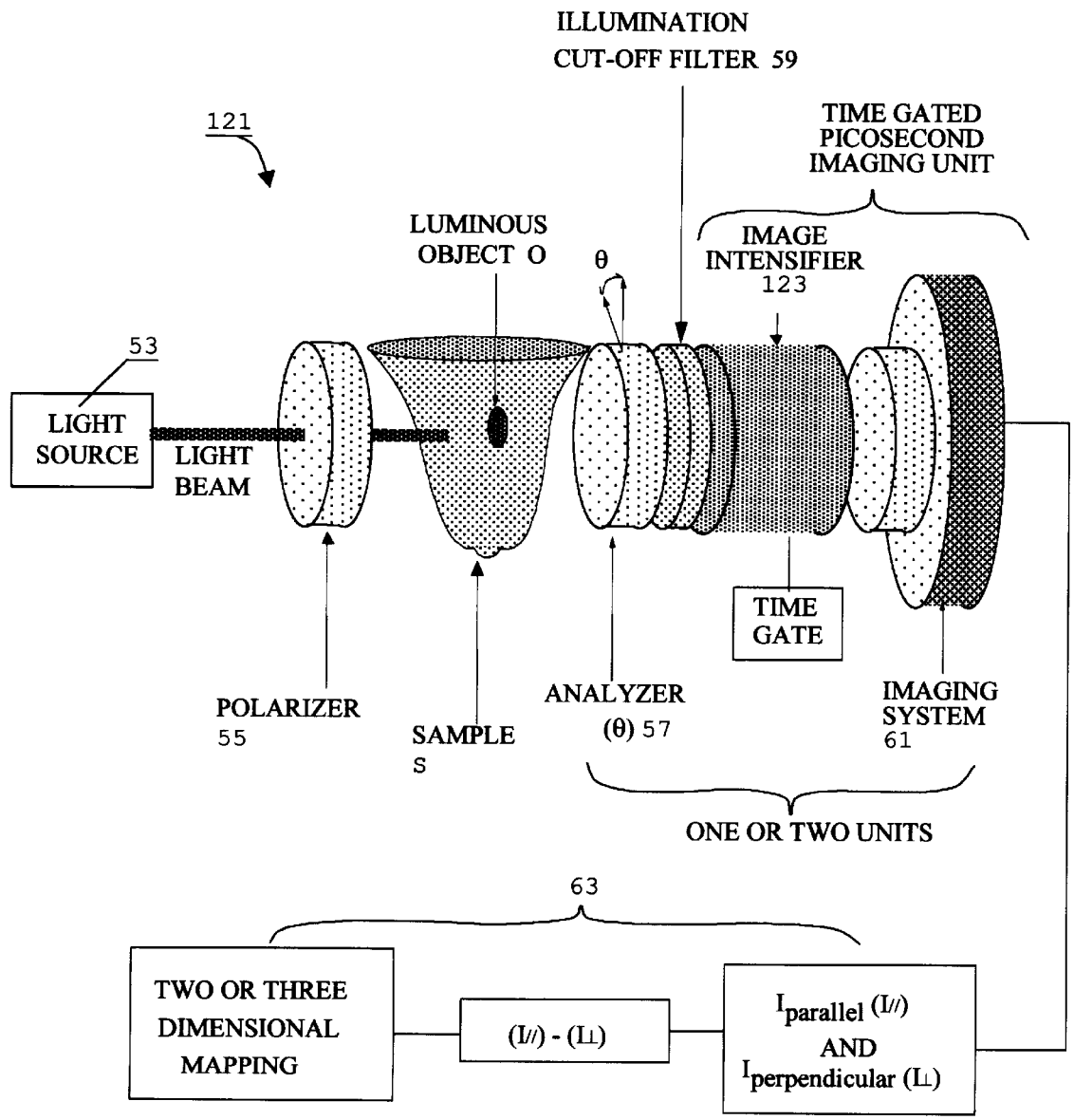
FIG. 9 is a schematic view of a fourth embodiment of a system for imaging an object in a turbid medium, the system being constructed according to the teachings of the present invention.

Referring now to FIG. 8, there is shown a schematic view of a third embodiment of a system constructed according to the teachings of the present invention for imaging an object in a turbid medium, the system being represented generally by reference numeral 101.

System 101 is identical to system 51, except that system 101 additionally includes a time and/or spatial gate 103 (e.g., Kerr gate or parametric gate or electronic gate and/or 4F Fourier spatial gate or another equivalent gating device) disposed between analyzer 57 and filter 59, gate 103 serving to preferentially pass early-arriving and forwardly-propagating photons of the emergent light from sample S.

Referring now to 9, there is a schematic view of a fourth embodiment of a system constructed according to the teachings of the present invention for imaging an object in a turbid medium, the system being represented generally by reference numeral 121.

System 121 is identical to system 51, except that system 121 additionally comprises an image intensifier 123 disposed between filter 59 and imaging system 61, image intensifier 123 being time gated and appropriately triggered to allow only the early part of the light emergent from the sample S to be amplified.

Figure 10:
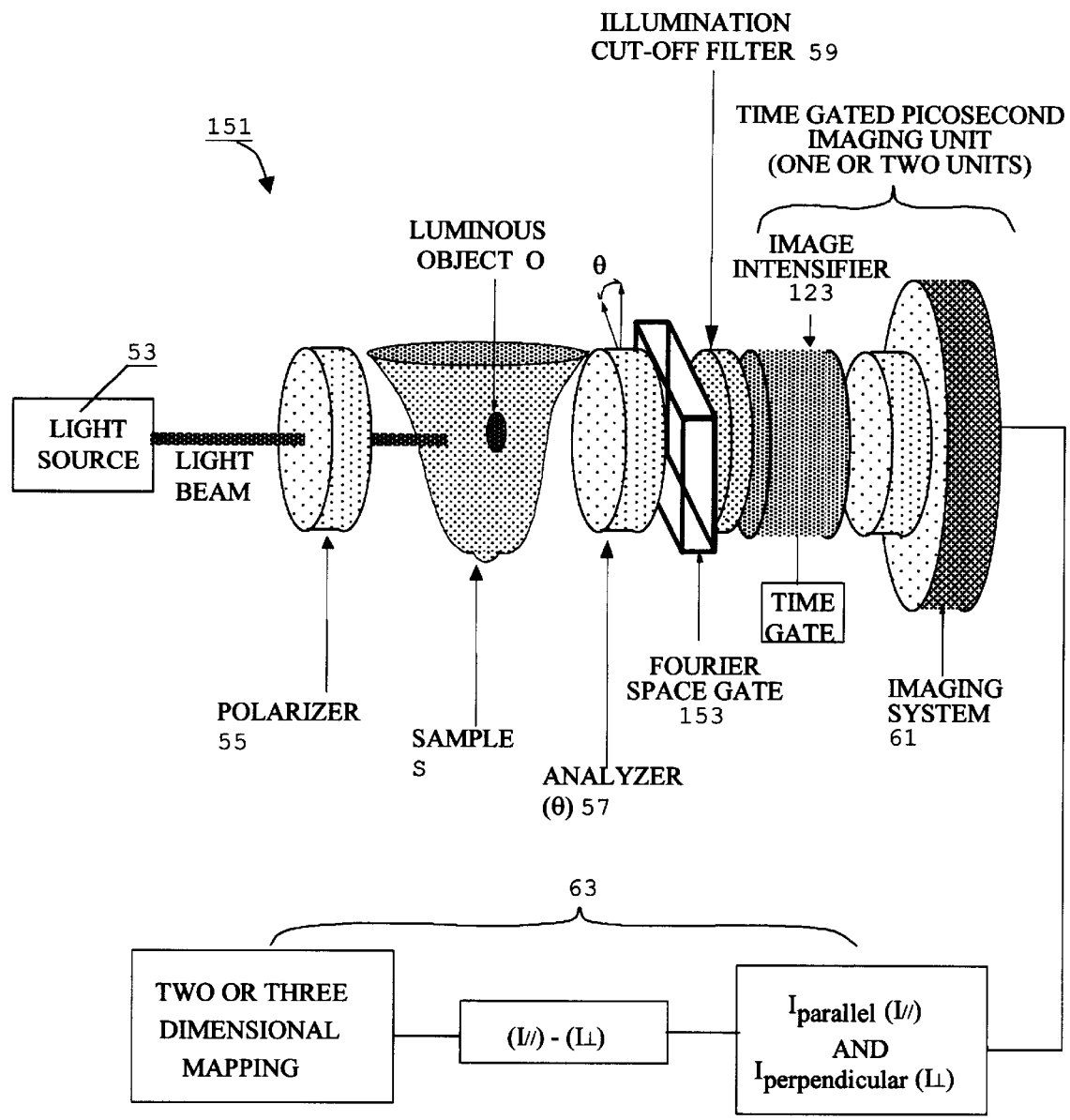
FIG. 10 is a schematic view of a fifth embodiment of a system for imaging an object in a turbid medium, the system being constructed according to the teachings of the present invention.

Referring now to FIG. 10, there is a schematic view of a fifth embodiment of a system constructed according to the teachings of the present invention for imaging an object in a turbid medium, the system being represented generally by reference numeral 151.

System 151 is identical to system 121, except that system 151 additionally includes a 4F Fourier space gate 153 disposed between analyzer 57 filter 59, space gate 153 serving to reduce the diffusive component of the light emergent from the sample S.

Figure 11A:
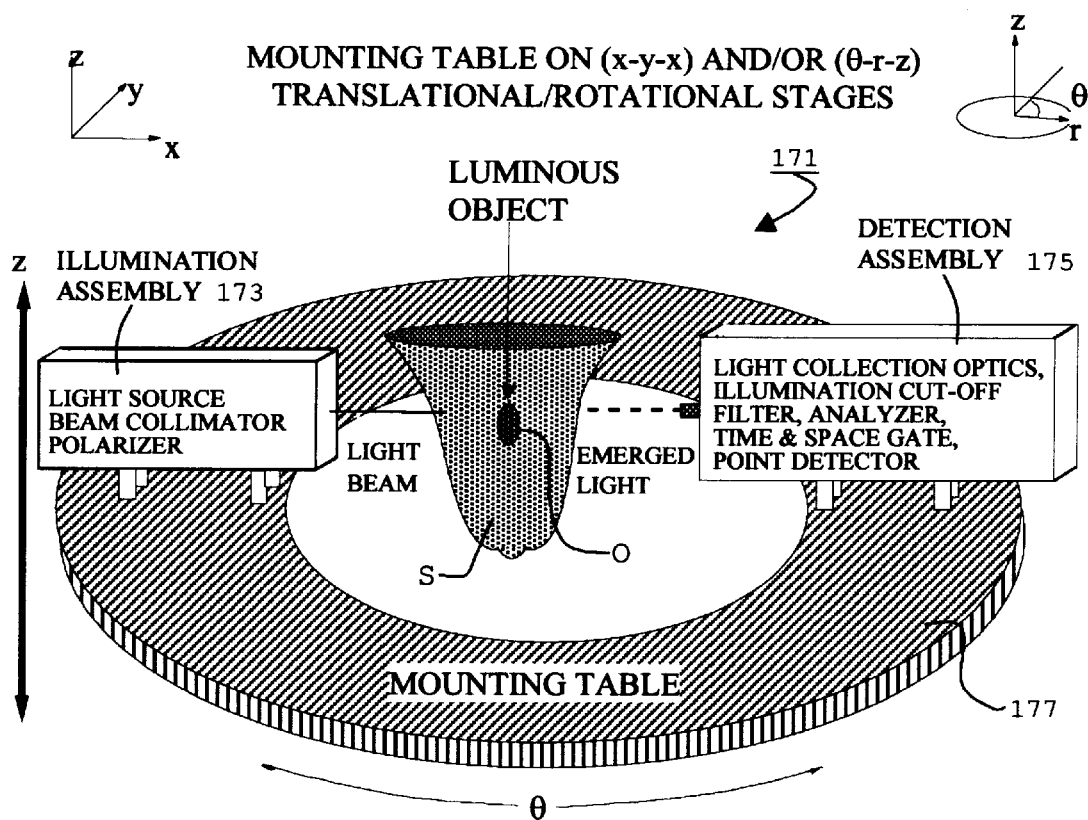
FIGS. 11(a) and 11(b) are schematic perspective and top views, respectively, of a sixth embodiment of a system for imaging an object in a turbid medium, the system being constructed according to the teachings of the present invention.
Figure 11B:
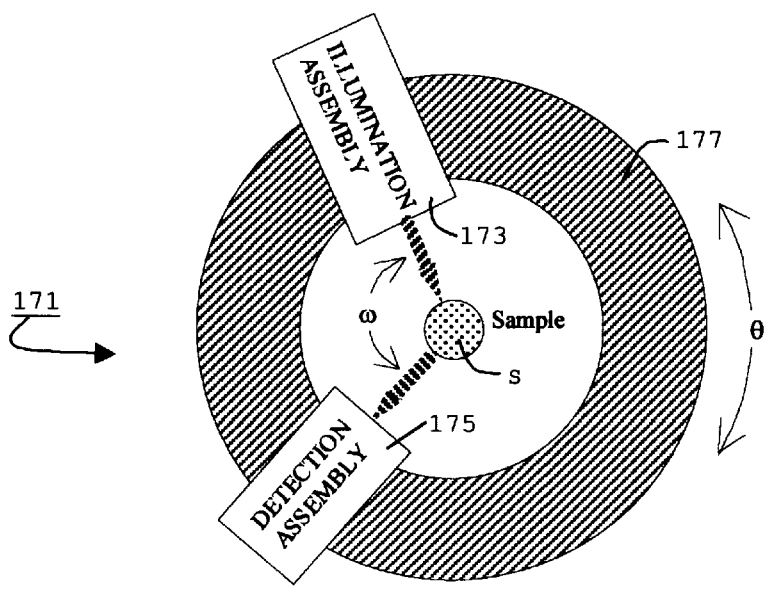

Referring now to FIGS. 11(a) and 11(b), there are schematic perspective and top views, respectively, of a sixth embodiment of a system constructed according to the teachings of the present invention for imaging an object in a turbid medium, the system being represented generally by reference numeral 171.

System 171 includes an illumination assembly 173, assembly 173 comprising a light source for producing a light beam, a beam collimator and a polarizer. The beam emitted from assembly 173 propagates through the sample S and photoexcites the luminescent object O. The light emergent from sample S enters into a detection assembly 175 placed at an angle $\omega$ with respect to the direction of illumination, $\omega$ having a value of between 0 and 360 degrees (e.g., 0 degrees for backscattering and 180 degrees for transmission geometry). Assembly 175 comprises light collection optics (lenses and/or mirrors), an analyzer, a time and/or spatial gate, a filter (holographic notch) used to block out the illuminating light, and a point detector (e.g., photodiode, photomultiplier). System 171 further includes a table 177 on which assemblies 173 and 175 are mounted, table 177 accommodating x-y-z and/or $\theta$-r-z translational/rotational stages to enable one to scan the sample S to obtain a point by point mapping. System 171 also includes electronics and computer software (not shown) for processing the parallel and perpendicular polarization measurements taken by assembly 175.

Figure 12A:
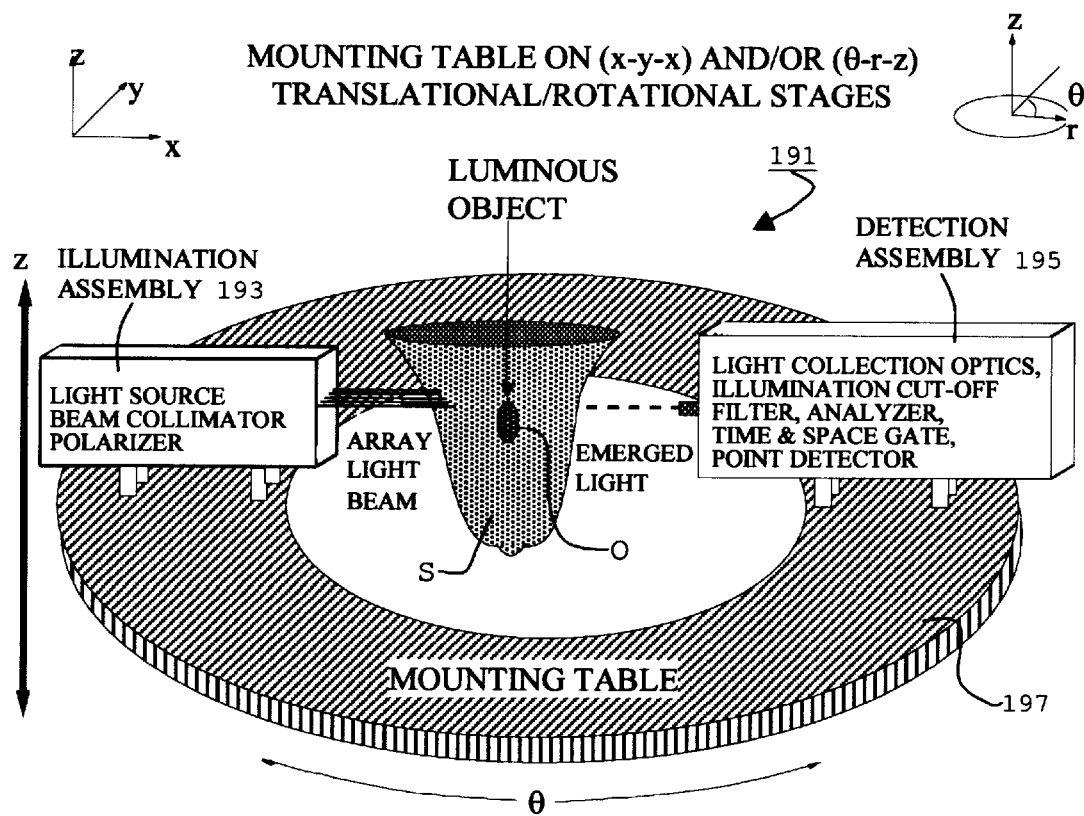
FIGS. 12(a) and 12(b) are schematic perspective and top views of a seventh embodiment of a system for imaging an object in a turbid medium, the system being constructed according to the teachings of the present invention.
Figure 12B:
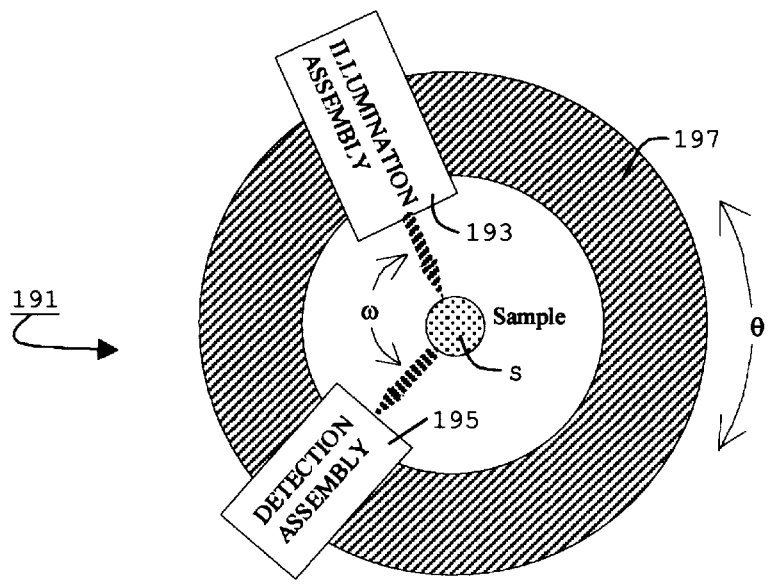

Referring now to FIGS. 12(a) and 12(b), there are shown schematic perspective and top views, respectively, of a seventh embodiment of a system constructed according to the teachings of the present invention for imaging an object in a turbid medium, the system being represented generally by reference numeral 191.

System 191 includes an illumination assembly 193, assembly 193 comprising a light source for producing a light beam array, a beam collimator and a polarizer. The beam array emitted from assembly 193 propagates through the sample S and photoexcites the luminescent object O. The light emergent from sample S enters into a detection assembly 195 placed at an angle ω with respect to the direction of illumination, ω having a value of between 0 and 360 degrees (e.g., 0 degrees for backscattering and 180 degrees for transmission geometry). Assembly 195 comprises light collection optics (lenses and/or mirrors), an analyzer, a time and/or spatial gate, a filter (holographic notch) used to block out the illuminating light, and an array detector. System 191 also includes a table 197, like table 177 of system 171, on which assemblies 193 and 195 are mounted and further includes electronics and computer software (not shown) for processing the parallel and perpendicular polarization measurements taken by assembly 195.

Figure 13A:
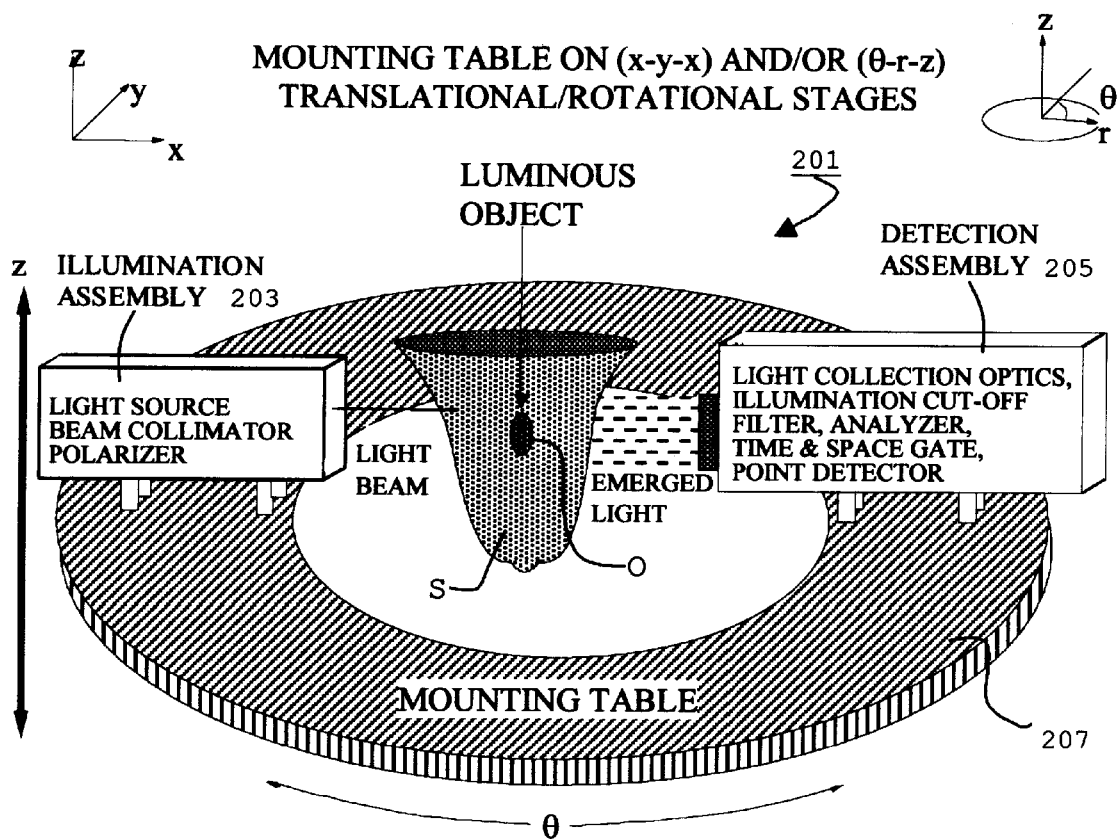
FIGS. 13(a) and 13(b) are schematic perspective and top views of an eighth embodiment of a system for imaging an object in a turbid medium, the system being constructed according to the teachings of the present invention.
Figure 13B:
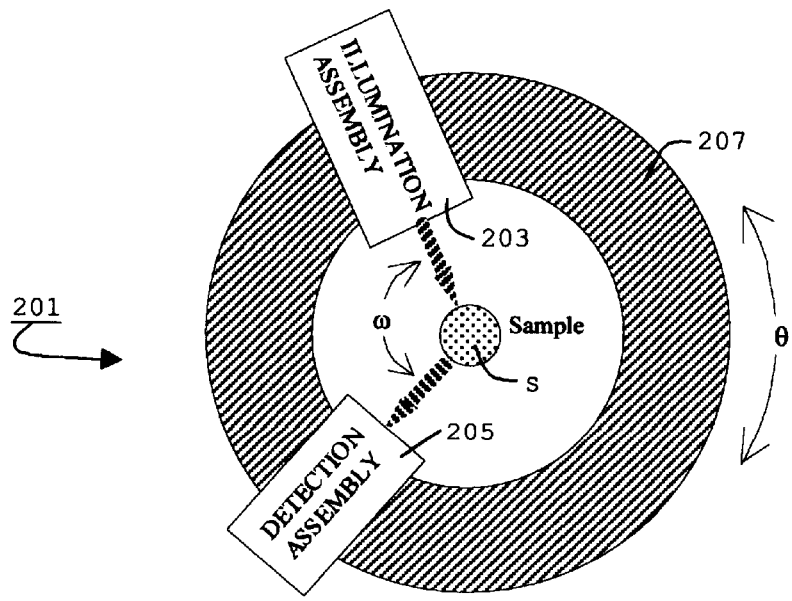

Referring now to FIGS. 13(a) and 13(b), there are shown schematic perspective and top views, respectively, of an eighth embodiment of a system constructed according to the teachings of the present invention for imaging an object in a turbid medium, the system being represented generally by reference numeral 201.

System 201 includes an illumination assembly 203, assembly 203 comprising a light source for producing a light beam, a beam collimator and a polarizer. The beam emitted from assembly 203 propagates through the sample S and photoexcites the luminescent object O. The light emergent from sample S enters into a detection assembly 205 placed at an angle ω with respect to the direction of illumination, ω having a value of between 0 and 360 degrees (e.g., 0 degrees for backscattering and 180 degrees for transmission geometry). Assembly 205 comprises light collection optics (lenses and/or mirrors), an analyzer, a time and/or spatial gate, a filter (holographic notch) used to block out the illuminating light, and a 2-dimensional detector. System 201 further includes a table 207, like table 177, on which assemblies 203 and 205 are mounted. System 201 also includes electronics and computer software (not shown) for processing the parallel and perpendicular polarization measurements taken by assembly 205.

Figure 14A:
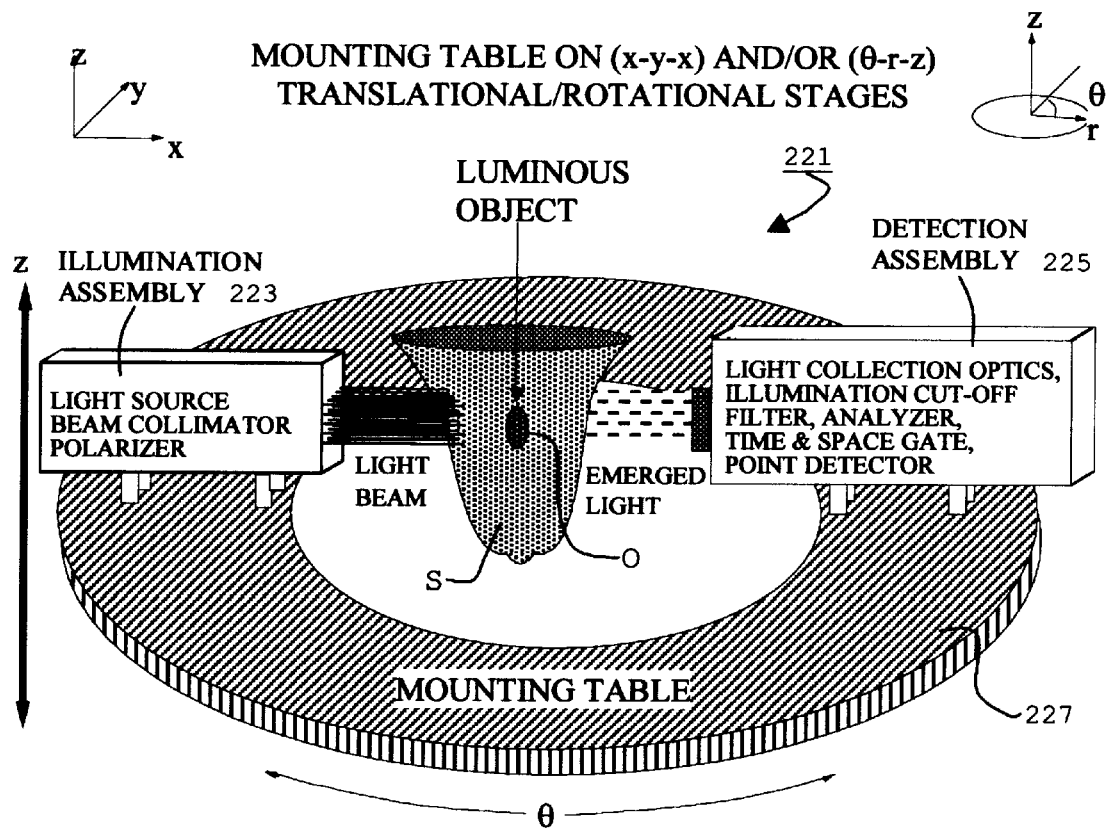
FIGS. 14(a) and 14(b) are schematic perspective and top views of a ninth embodiment of a system for imaging an object in a turbid medium, the system being constructed according to the teachings of the present invention.
Figure 14B:
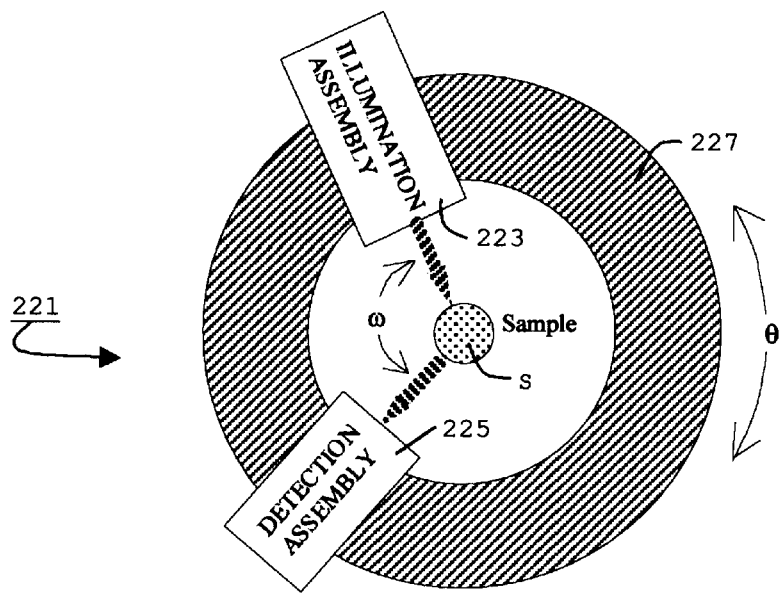

Referring now to FIGS. 14(a) and 14(b), there are shown schematic perspective and top views, respectively, of a ninth embodiment of a system constructed according to the teachings of the present invention for imaging an object in a turbid medium, the system being represented generally by reference numeral 221.

System 221 includes an illumination assembly 223, assembly 223 comprising a light source for producing a light beam, a beam collimator, a beam expander for illuminating a large area of a sample and a polarizer. The beam emitted from assembly 223 propagates through the sample S and photoexcites the luminescent object O. The light emergent from sample S enters into a detection assembly 225 placed at an angle ω with respect to the direction of illumination, ω having a value of between 0 and 360 degrees (e.g., 0 degrees for backscattering and 180 degrees for transmission geometry). Assembly 225 comprising light collection optics (lenses and/or mirrors), an analyzer, a time and/or spatial gate, a filter (holographic notch) used to block out the illuminating light, and a 2-dimensional detector. System 221 further includes a table 227, like table 177, on which assemblies 223 and 225 are mounted. System 221 also includes electronics and computer software (not shown) for processing the parallel and perpendicular polarization measurements taken by assembly 225.

Figure 15:
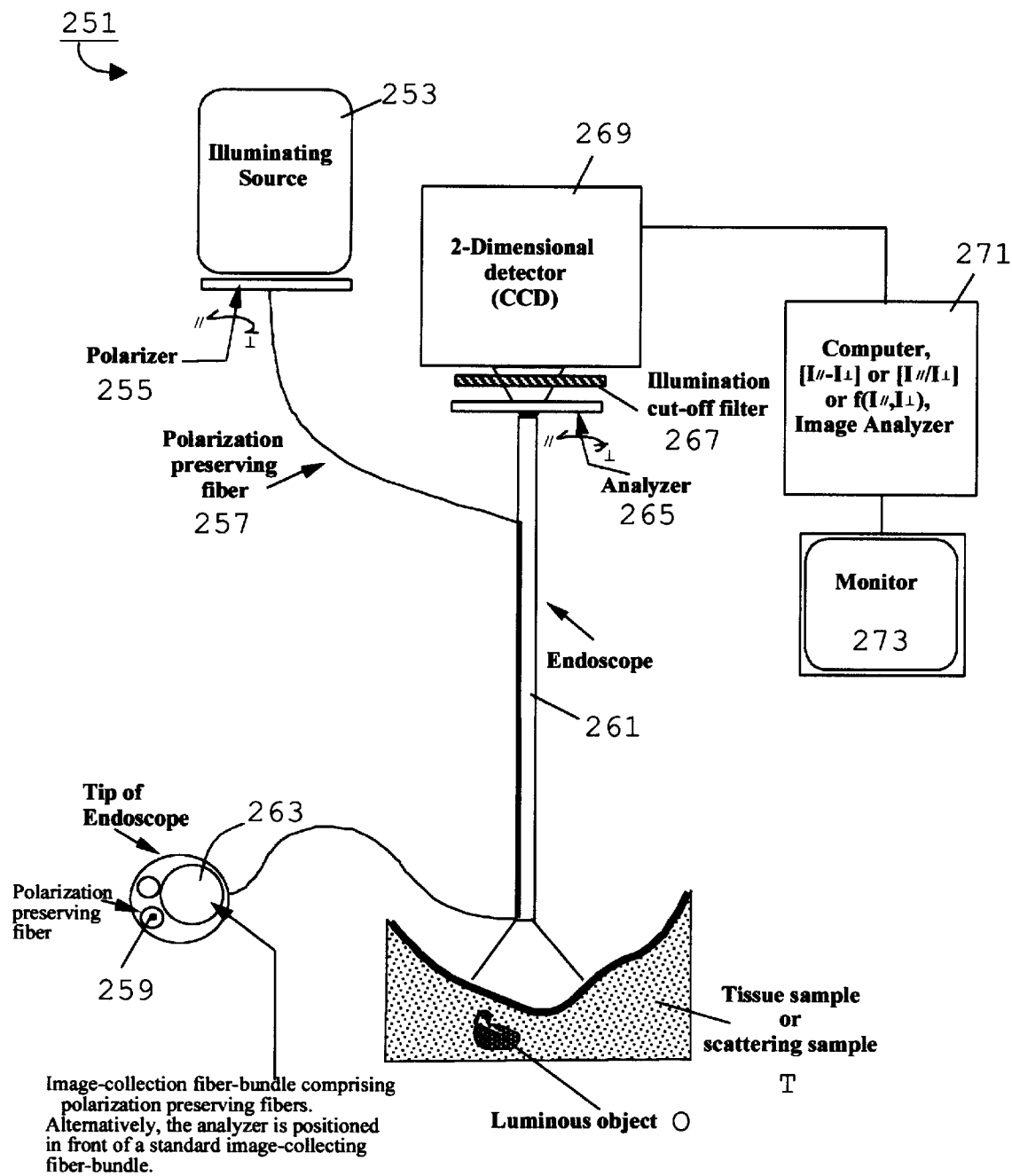
FIG. 15 is a schematic view of a tenth embodiment of a system for imaging an object in a turbid medium, the system being constructed according to the teachings of the present invention.

Referring now to FIG. 15, there is shown a schematic view of a tenth embodiment of a system constructed according to the teachings of the present invention for imaging an object in a turbid medium, the system being represented generally by reference numeral 251.

System 251 includes an illuminating source 253, which may be the same as source 53 of system 51. System 251 also includes a rotatably mounted polarizer 255, which is used to ensure that the light emitted from source 253 is polarized. System 251 also includes a polarization preserving fiber 257, into which the aforementioned polarized light is inputted. Fiber 257, in turn, is disposed within a working channel 259 of an endoscope 261. The light transmitted by fiber 257 may be used to illuminate a tissue sample T having a luminous object disposed therein. The backscattered light from tissue sample T is collected by an image-collection fiber bundle 263 disposed within endoscope 261. A rotatably-mounted analyzer 265 is located at the distal end of bundle 263 and is used to select the parallel and perpendicular components of the backscattered light. (As can readily be appreciated, either polarizer 255 can be placed in the parallel position while analyzer 265 is placed in the parallel and perpendicular positions or vice versa.) The light passed through analyzer 265 is then passed through a filter 267, which blocks out light of the illuminating wavelength, and is detected by a 2-dimensional detector 269. The output of detector 269 is then transmitted to a computer 271, which processes the parallel and perpendicular polarization measurements and forms a difference image, which is then displayed on a monitor 273.

Figure 16:
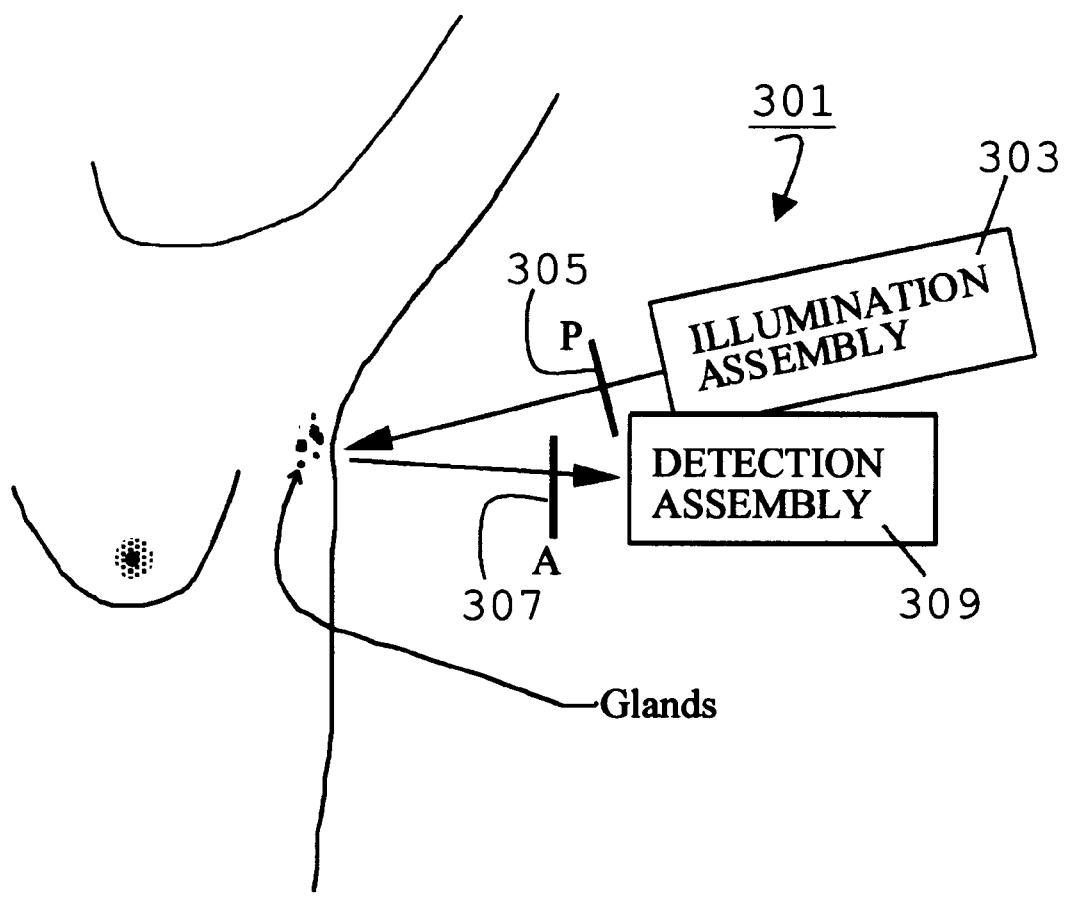
FIG. 16 is a schematic view of a system constructed according to the teachings of the present invention that is designed for imaging, in a woman, the glands located under the arm for the detection of a precancerous or cancerous condition therein.

Referring now to FIG. 16, there is a schematic view of a system constructed according to the teachings of the present invention that is designed for imaging, in a woman, the glands located under the arm for the detection of a precancerous or cancerous condition therein, the system being represented generally by reference numeral 301.

System 301 includes an illuminating assembly 303, assembly 303 including a light source for emitting a beam of light and means for collimating and expanding said beam of light. System 301 also includes a polarizer 305 for polarizing the light emitted from assembly 303. The light passed through polarizer 305 is then used to illuminate the tissue in question, i.e., a gland to which a luminescent contrast agent that preferentially binds to cancerous or precancerous tissue has previously been added. System 301 additionally includes an analyzer 307 through which the luminescent light emergent from the glandular tissue is passed. System 301 further includes a detection assembly 309. Detection assembly 309 includes appropriate optical elements (lenses and/or mirrors) to collect the light, a time and/or spatial gate, a filter (holographic notch) to block the illuminating wavelength and a two-dimensional detector to record the image of the luminous object. Point-by-point or over-area imaging may be used.

Figure 17:
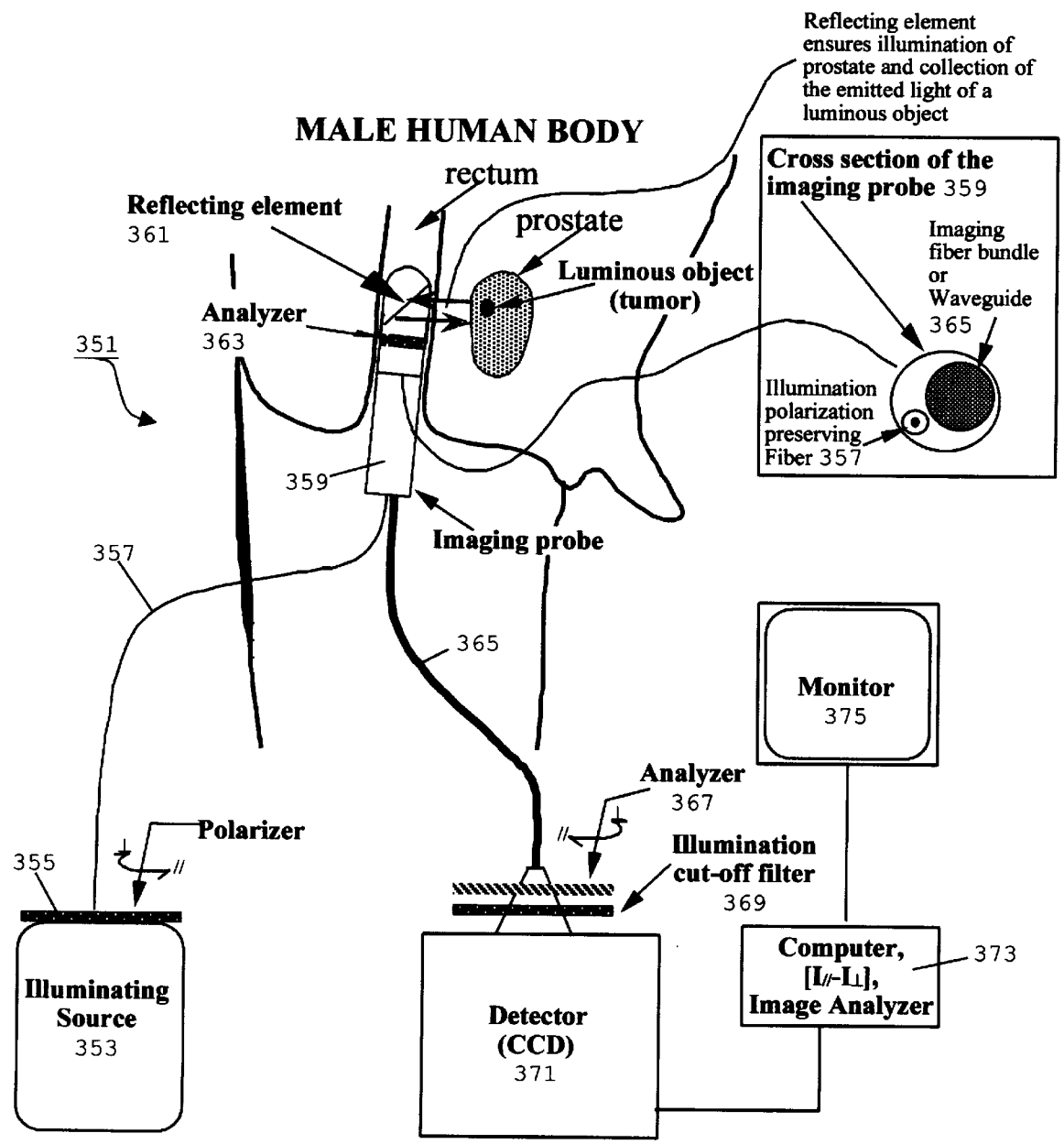
FIG. 17 is a schematic view of a system constructed according to the teachings of the present invention that is designed for imaging the prostate gland for the detection of a precancerous or cancerous condition therein.

Referring now to FIG. 17, there is a schematic view of a system constructed according to the teachings of the present invention that is designed for imaging the prostate gland for the detection of a precancerous or cancerous condition therein, the system being represented generally by reference numeral 351.

System 351 includes an illuminating source 353, which may be the same as source 253 of system 251. System 351 also includes a rotatably mounted polarizer 355, which is used to ensure that the light emitted from source 353 is polarized. System 351 also includes a polarization preserving fiber 357, into which the aforementioned polarized light is inputted. Fiber 357, in turn, is disposed within an imaging probe 359 adapted to be inserted into a rectum. A reflecting element 361 and an analyzer 363 are disposed within imaging probe 359. Reflecting element 361 is used to direct the illuminating light from fiber 357 onto the prostate tissue being examined (to which a luminescent contrast agent that preferentially binds to cancerous or precancerous tissue has previously been added) and to direct the light emitted from the illuminated prostate tissue first through analyzer 363 and then into an imaging fiber (for point-by-point imaging) or imaging fibers (for over-area imaging) 365 also disposed within imaging probe 359. A rotatably-mounted analyzer 367 is located at the distal end of bundle 365 and is used to select the parallel and perpendicular components of the backscattered light. (As can readily be appreciated, either polarizer 355 can be placed in the parallel position while analyzer 367 is placed in the parallel and perpendicular positions or vice versa.) The light passed through analyzer 367 is then passed through a holographic notch filter 369, which blocks out light of the illuminating wavelength, and is detected by a 2-dimensional detector 371. (A 1-dimensional detector could be used instead of detector 371 if point-by-point imaging is desired.) The output of detector 371 is then transmitted to a computer 373, which processes the parallel and perpendicular polarization measurements and forms a difference image, which is then displayed on a monitor 375.

As is apparent from the discussion above, for purposes of the present invention, the light emitted by the luminous object may be imaged by the detector at any angle with respect to the illumination and independently of the way the luminous object was photoexcited. The most useful imaging geometry, which is possibly more suitable for medical imaging applications, is a backscattering geometry. The object located inside the scattering medium (i.e., underneath the surface of a tissue for medical applications) is illuminated, and the backscattered light emitted by the luminous object is collected to form the image of the object. The fluorescence polarization difference technique of the present invention may then be used to cancel out the diffusive component of the fluorescent light for improved image quality.

In human breast tissue samples, polarization is preserved for tissue thicknesses of more than 1 cm. Therefore, the technique of the present invention may be useful in medical imaging, especially when the backscattering geometry is used for subsurface imaging. The contrast agents to be used for medical imaging have all the properties discussed above and, in addition, bind to molecules associated and/or involved in tumors, cancers, brain disorders, liver disorders or other disorders or diseases of the human body. Such contrast agents, when injected into the human body, will concentrate themselves primarily in the diseased parts of the human body; therefore, using the present technique, images of the diseased parts of the human body can be obtained.

By practicing the present technique in a backscattering geometry, one can examine the emission from a contrast agent associated with a disease located in the glands under the arm, such as for breast cancer screening. The backscattering geometry can also be used to detect diseases or disorders in the prostate by inserting an appropriate imaging probe in the rectum. Photoactive drugs could be tailored to be used as contrast agents for a wide range of diseases, the drugs being capable of being absorbed by diseased tissues and emitting light in the NIR spectral region.

Figure 18:
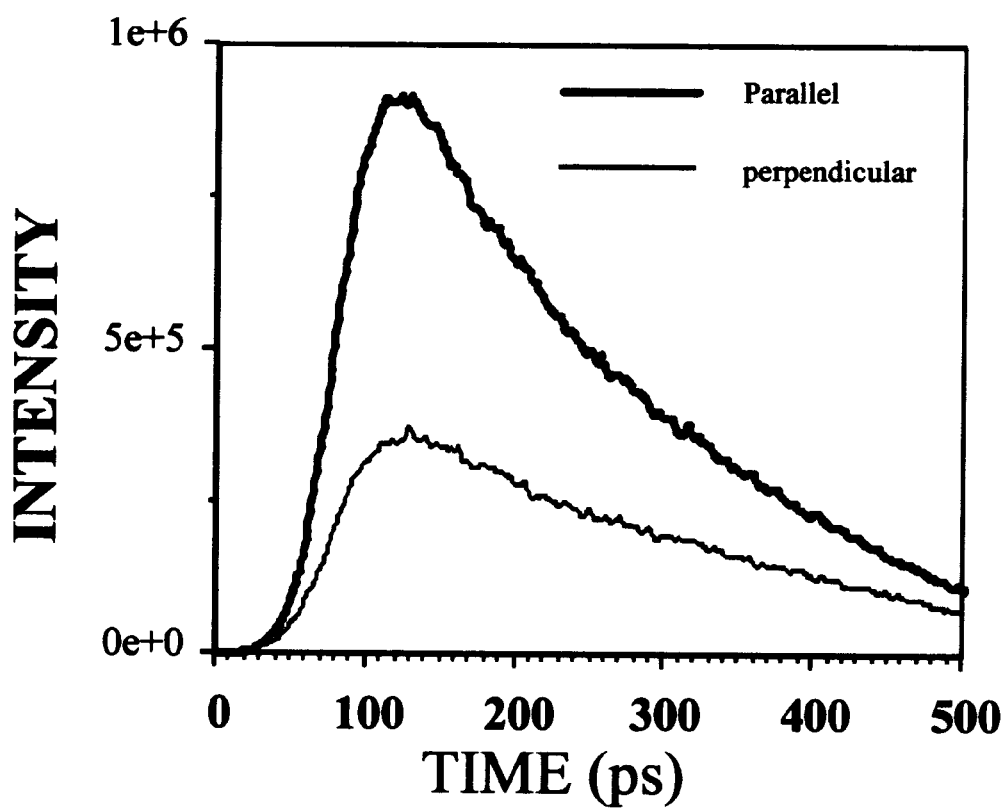
FIG. 18 is a graphic representation of the parallel and perpendicular components of the luminescence, over time, of the contrast agent Cardio Green in water following 630 nm excitation.

We have tested the above concepts in tissues using the dye Cardio Green as the contrast agent. Cardio Green exhibits strong absorption in the 720–820 nm spectral region and emits in the 800–860 nm spectral region. The emission of Cardio Green following polarized illumination is strongly polarized while its decay time is on the order of 200 ps. The parallel and perpendicular components of Cardio Green fluorescence, over time, are shown in FIG. 18. As can be seen, Cardio Green has all the appropriate absorption and emission characteristics in order to be used for optical imaging in tissues to test the concepts of this invention.

Figure 19:
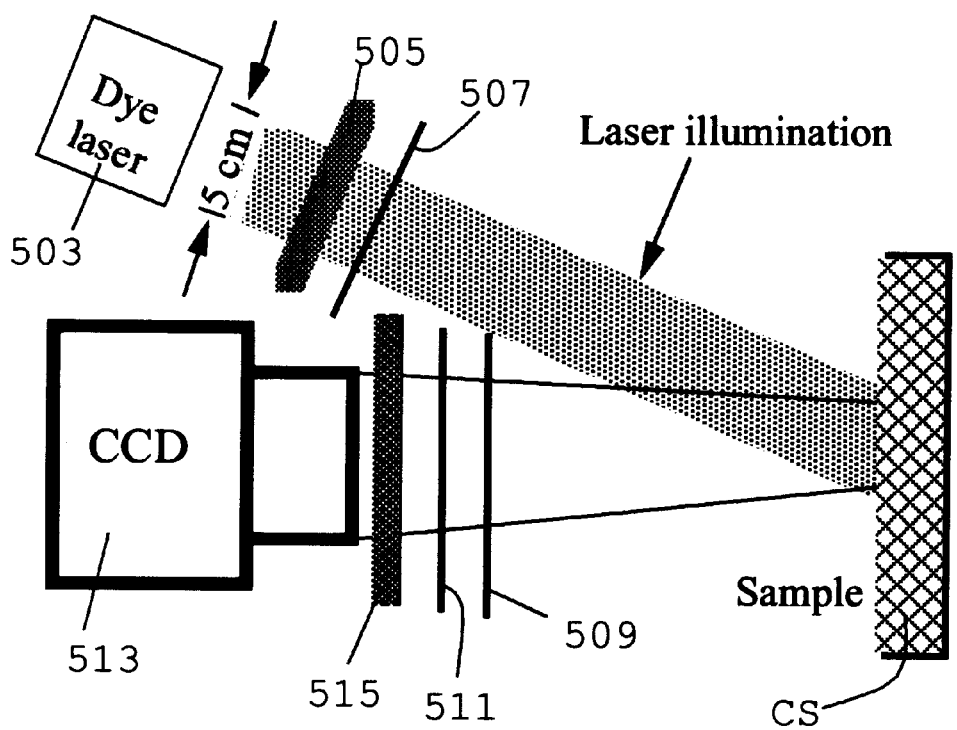
FIG. 19 is a simplified schematic view of an experimental setup used for imaging, in a backscattering geometry, a chicken breast tissue sample comprising a pair of chicken breast tissue pieces dyed with Cardio Green and then positioned 1.5 mm apart on top of a 2 cm thick chicken breast tissue slab and beneath a 2 mm thick chicken breast tissue slab.
Figure 20:
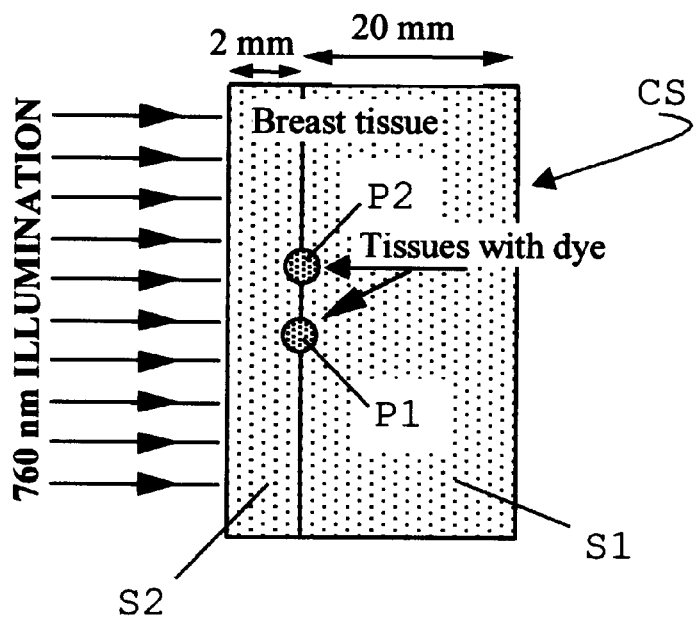
FIG. 20 is an enlarged schematic section view of the chicken breast tissue sample of FIG. 19.

Referring now to FIGS. 19 and 20, there are shown (i) a simplified schematic view of an experimental setup which was used to image, in a backscattering geometry, a chicken breast tissue sample CS comprising a pair of chicken breast tissue pieces P1 and P2 dyed for about 5 seconds with Cardio Green and then positioned 1.5 mm apart on top of a 2 cm thick chicken breast tissue slab S1, which was then covered with a 2 mm thick chicken breast tissue slab S2 and (ii) an enlarged schematic section view of said chicken breast tissue sample CS, respectively.

A dye laser 503 was used to emit a laser beam at 760 nm. The laser beam was expanded by means (not shown) to provide spatially broad and reasonably uniform illumination. A polarizer 505 was used to ensure that the laser beam was linearly polarized and a narrow band laser line filter 507 was used to ensure that the laser beam was monochromatic. As seen best in FIG. 20, the laser beam illuminated the sample CS from the direction of the 2 mm chicken breast tissue slab S2.

The fluorescent light emitted by the dyed pieces P1 and P2 was collected in a near-backscattering geometry. A laser line notch filter 509 and an 830 nm long pass filter 511 were used to ensure that only the fluorescent light due to Cardio Green was passed to a CCD detector 513. A rotatably-mounted analyzer 515 was positioned in front of detector 513 so that the parallel and perpendicular image components could be obtained.

Figure 21A:
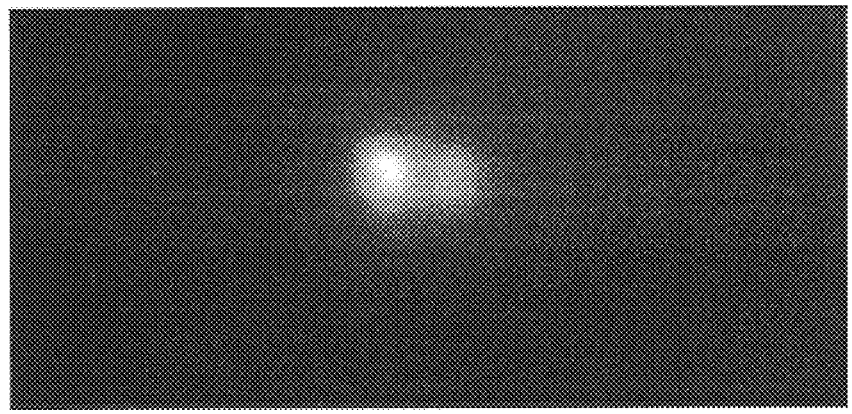
FIGS. 21(a) through 21(c) are images of the sample of FIG. 20 obtained using the setup of FIG. 19, the images being formed of (a) the parallel component of the luminescent light, (b) the perpendicular component of the luminescent light and (c) the difference of the parallel and perpendicular components of the luminescent light, respectively.
Figure 21B:
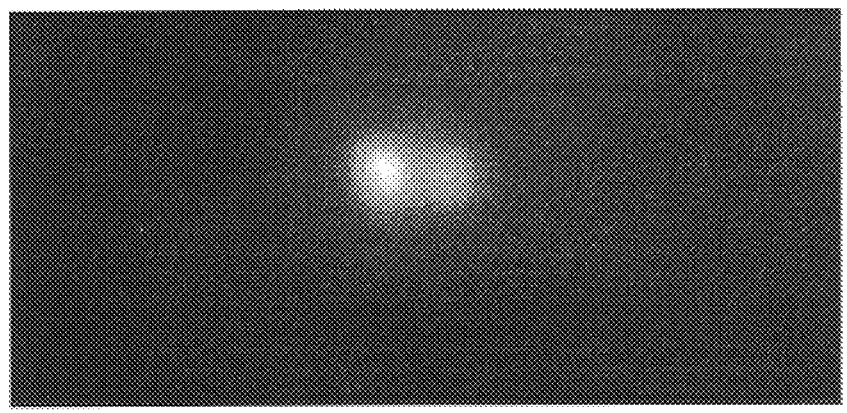
Figure 21C:
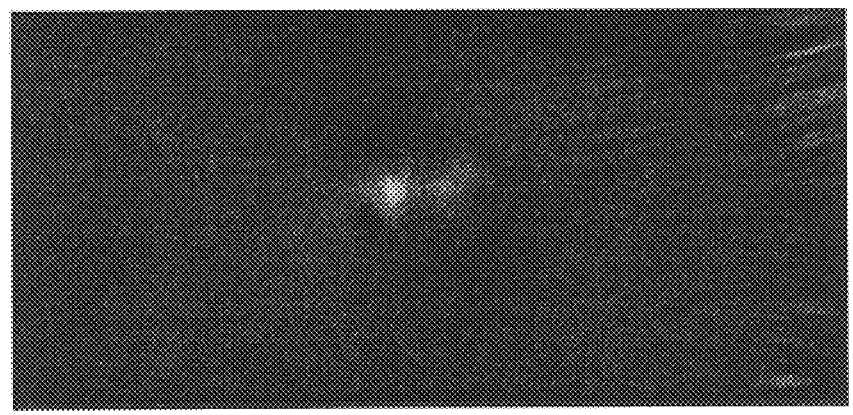
Figure 22:
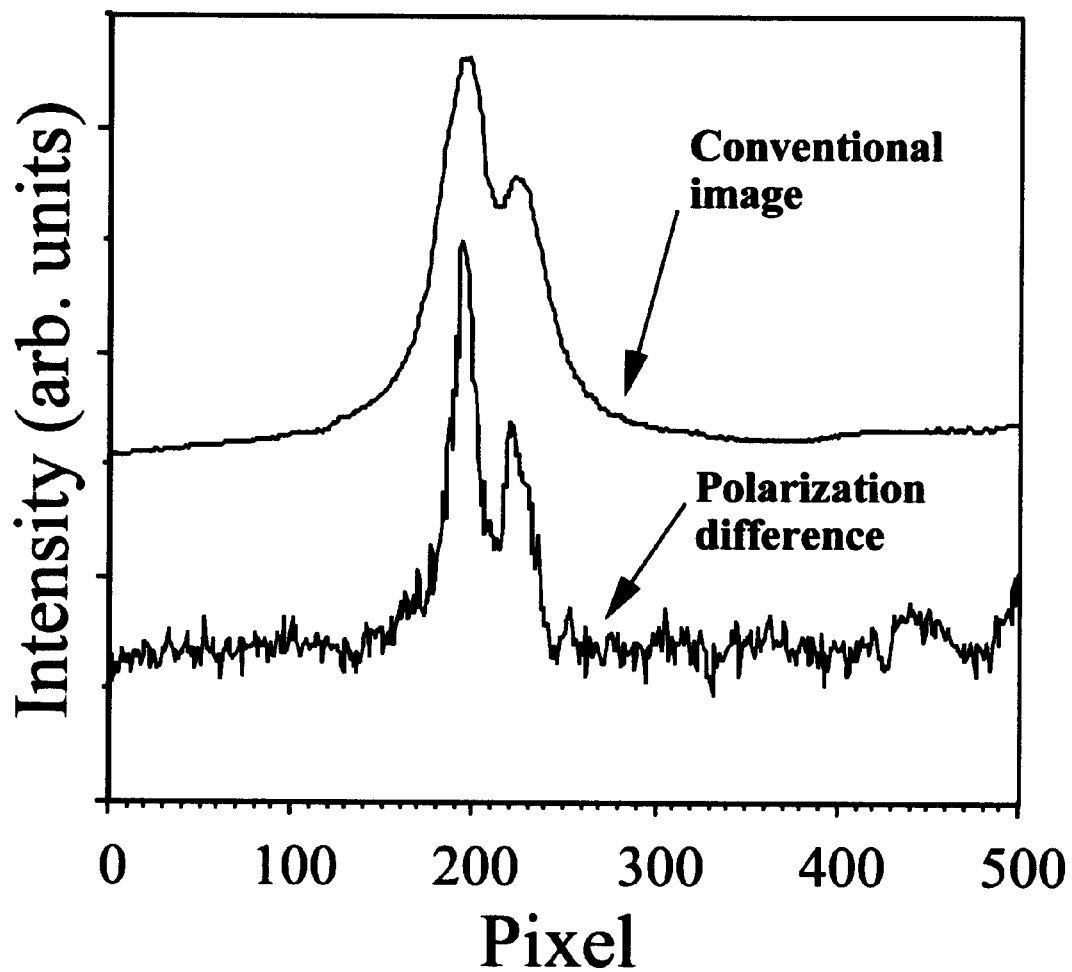
FIG. 22 is a graphic representation of the digitized intensity profiles, across a line containing the two luminous objects, of the image of FIG. 21(c) and of a corresponding conventional image taken without the use of polarizers.

Referring now to FIGS. 21(a) through 21(c), there can be seen the parallel polarization image, the perpendicular polarization image and the polarization difference image, respectively, of the sample of FIG. 20 obtained using the setup of FIG. 19. The improvement in the image resolution is demonstrated in FIG. 22, where there is shown a lower digitized intensity profile, which corresponds to the intensity of an image across a line containing the two emitting tissue samples where the polarization difference technique of the present invention was used, and an upper digitized intensity profile, which corresponds to the intensity of an image across a line containing the two emitting tissue samples where no polarizers were used. As can be seen, the two peaks are much better resolved in the lower profile due to the improvement in image resolution made possible by the present invention.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for imaging an object located in a turbid medium, said method comprising the steps of:
   (a) making the object luminescent by adding to the object a contrast agent of the type that emits at least partially polarized light when appropriately excited with polarized radiation;
   (b) exciting the luminescent object through the turbid medium with polarized radiation so as to cause luminescent light to be emitted from the luminescent object, said luminescent light initially being at least partially polarized;
   (c) after said luminescent light has emerged from the turbid medium, said luminescent light consisting of a ballistic component, a snake-like component and a diffuse component, detecting a pair of complementary polarization components of said luminescent light; and
   (d) forming an image of the object using the pair of complementary polarization components.

2. The method as claimed in claim 1 wherein the turbid medium is a tissue sample.

3. The method as claimed in claim 2 wherein the tissue sample is a human tissue sample.

4. The method as claimed in claim 3 wherein the human tissue sample is selected from the group consisting of human breast tissue, human brain tissue, human prostate tissue, human liver tissue, human skin tissue, human gastrointestinal tissue, human mucosa tissue, human GYN tissue, human under-arm glandular tissue and human kidney tissue.

5. The method as claimed in claim 4 wherein the human tissue sample is human breast tissue.

6. The method as claimed in claim 1 wherein the exciting polarized radiation is selected from the group consisting of exciting polarized light, X-rays and particle beam.

7. The method as claimed in claim 6 wherein the exciting polarized radiation is photoexciting polarized light.

8. The method as claimed in claim 7 wherein the exciting polarized radiation has a wavelength that exhibits minimum absorption in tissues.

9. The method as claimed in claim 7 wherein the exciting polarized radiation has a wavelength in the 700 to 1600 nm spectral region.

10. The method as claimed in claim 7 wherein the exciting polarized radiation is produced by a laser selected from the group consisting of semiconductor, Ti:Sapphire, Forsterite, Cr:YAG and Nd:YAG lasers.

11. The method as claimed in claim 7 wherein the photoexciting polarized light is selected from the group consisting of pulsed and continuous wave lamp and laser light.

12. The method as claimed in claim 11 wherein the photoexciting polarized light is pulsed laser light.

13. The method as claimed in claim 7 wherein the photoexciting polarized light is linearly polarized and wherein said pair of complementary polarization components are parallel and perpendicular to the photoexciting polarized light.

14. The method as claimed in claim 13 wherein said forming step comprises calculating one of a ratio, a difference and a combination of a ratio and a difference of the pair of complementary polarization components and using said ratio, difference or combination to form said image.

15. The method as claimed in claim 14 wherein said ratio, difference or combination is selected from the group consisting of $I_\parallel - I_\perp$, $I_\parallel/I_\perp$, $(I_\parallel - I_\perp)/(I_\parallel + I_\perp)$, $(I_\perp)/(I_\parallel - I_\perp)$, $(I_\parallel - I_\perp)/(I_\perp)$, and $(I_\parallel - I_\perp)/(I_\parallel)$.

16. The method as claimed in claim 1 wherein said contrast agent is selected from the group consisting of dyes, phosphors, dielectrics, ceramics, semiconductors and impurity-doped materials.

17. The method as claimed in claim 16 wherein said contrast agent is selected from the group consisting of Eosin, Rose Begal, Cardio Green, photofrin, HPD, porphyrin derivative dyes and TCTIF.

18. The method as claimed in claim 1 wherein said contrast agent is Eosin.

19. The method as claimed in claim 1 wherein said contrast agent, when excited, emits at least partially polarized light with an optical relaxation time in the range of 50 ps to 5 $\mu$s.

20. The method as claimed in claim 1 wherein said contrast agent, when excited, emits light in the spectral region between 400 and 1600 nm.

21. The method as claimed in claim 1 wherein the turbid medium is a tissue and wherein said contrast agent, when excited, emits light in the absorption range of the tissue.

22. The method as claimed in claim 1 wherein the turbid medium is a tissue and wherein said contrast agent preferentially binds to malignant, as opposed to non-malignant, tissue.

23. The method as claimed in claim 1 wherein the contrast agent is of the type that preferentially binds to molecules associated with cancers, disorders or diseases of the human body.

24. The method as claimed in claim 1 wherein said detecting step comprises passing the light that emerges from the turbid medium through analyzer means and a filter for selectively passing the luminescent light and then measuring the intensity of the thus passed light.

25. A method for imaging an object located in a turbid medium, said method comprising the steps of:
   (a) making the object luminescent by adding to the object a contrast agent of the type that emits at least partially polarized light when appropriately excited with polarized radiation;
   (b) exciting the luminescent object through the turbid medium with exciting polarized radiation so as to cause luminescent light to be emitted from the luminescent object, said luminescent light initially being at least partially polarized;
   (c) passing the light that emerges from the turbid medium through analyzer means for selectively transmitting therethrough a pair of complementary polarization components of said emergent light;
   (d) passing the pair of complementary polarization components through a filter for selectively passing therethrough luminescent light of said pair of complementary polarization components;
   (e) detecting the thus filtered pair of complementary polarization components; and
   (f) forming an image of the object using the detected pair of complementary polarization components.

26. The method as claimed in claim 25, further comprising the step of gating the luminescent light that has emerged from the turbid medium to preferentially pass the ballistic and snake components thereof, said gating step comprising at least one of time gating and space gating the luminescent light that has emerged from the turbid medium to preferentially pass the ballistic and snake components thereof.

27. The method as claimed in claim 26, wherein said gating is performed after said analyzing step and before said detecting step.

28. A method for imaging an object located in a turbid medium, said method comprising the steps of:
  (a) making the object luminescent by adding to the object a contrast agent of the type that emits polarized light when appropriately excited;
  (b) exciting the luminescent object through the turbid medium with exciting radiation so as to cause luminescent light to be emitted from the luminescent object, said luminescent light initially being polarized;
  (c) after said luminescent light has emerged from the turbid medium, said luminescent light consisting of a ballistic component, a snake-like component and a diffuse component, detecting a pair of complementary polarization components of said luminescent light; and
  (d) forming an image of the object using the pair of complementary polarization components.

29. The method as claimed in claim 28, wherein the turbid medium is a tissue sample.

30. The method as claimed in claim 29, wherein the tissue sample is a human tissue sample.

31. The method as claimed in claim 30, wherein the human tissue sample is selected from the group consisting of human breast tissue, human brain tissue, human prostate tissue, human liver tissue, human skin tissue, human gastrointestinal tissue, human mucosa tissue, human GYN tissue, human under-arm glandular tissue and human kidney tissue.

32. The method as claimed in claim 31, wherein the human tissue sample is human breast tissue.

33. The method as claimed in claim 28, wherein the exciting radiation is selected from the group consisting of light, X-rays and particle beam.

34. The method as claimed in claim 33, wherein the exciting radiation is photoexciting light.

35. The method as claimed in claim 34, wherein the photoexciting light is selected from the group consisting of pulsed and continuous wave lamp and laser light.

36. The method as claimed in claim 35, wherein the photoexciting light is pulsed laser light.

37. The method as claimed in claim 28, wherein the contrast agent emits linearly polarized luminescent light and wherein said pair of complementary polarization components are parallel and perpendicular to the linearly polarized luminescent light.

38. The method as claimed in claim 37, wherein said forming step comprises calculating one of a ratio, a difference and a combination of a ratio and a difference of the pair of complementary polarization components and using said ratio, difference or combination to form said image.

39. The method as claimed in claim 38 wherein said ratio, difference or combination is selected from the group consisting of $I_\parallel - I_\perp$, $I_\parallel / I_\perp$, $[I_\parallel - I_\perp]/[I_\parallel + I_\perp]$, $[I_\perp]/[I_\parallel - I_\perp]$, $[I_\parallel - I_\perp]/[I_\perp]$, and $[I_\parallel - I_\perp]/[I_\parallel]$.

40. The method as claimed in claim 28, wherein said detecting step comprises passing the light that emerges from the turbid medium through analyzer means and a filter for selectively passing the luminescent light and then measuring the intensity of the thus passed light.

41. The method as claimed in claim wherein 40 wherein the contrast agent is of the type that preferentially binds to molecules associated with cancers, disorders or diseases of the human body.

* * * * *